(12) United States Patent
Usuda et al.

(10) Patent No.: US 6,673,576 B1
(45) Date of Patent: Jan. 6, 2004

(54) PROCESS FOR PRODUCING NUCLEIC ACIDS

(75) Inventors: Yoshihiro Usuda, Kawasaki (JP); Hisashi Kawasaki, Kawasaki (JP); Megumi Shimaoka, Kawasaki (JP); Takashi Utagawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 08/913,816

(22) PCT Filed: Mar. 22, 1996

(86) PCT No.: PCT/JP96/00761

§ 371 (c)(1),
(2), (4) Date: May 13, 1998

(87) PCT Pub. No.: WO96/30501

PCT Pub. Date: Oct. 3, 1996

(30) Foreign Application Priority Data

Mar. 24, 1995 (JP) .............................. 7-102888
Jun. 9, 1995 (JP) .............................. 7-177900

(51) Int. Cl.$^7$ .......................... C12D 19/30; C12N 9/16; C12N 1/20; C07H 21/04
(52) U.S. Cl. ...................... 435/89; 435/196; 435/252.3; 435/252.32; 435/252.33; 435/320.1; 435/69.1; 536/23.2
(58) Field of Search ........................ 435/89, 196, 252.3, 435/252.32, 252.33, 320.1, 69.1; 536/23.2

(56) References Cited

U.S. PATENT DOCUMENTS 5,756,315 A * 5/1998 Mori et al. .................... 435/89

FOREIGN PATENT DOCUMENTS

| EP | 0 282 989 | 3/1988 |
| EP | 0 458 971 | 12/1991 |
| JP | 39-29858 | 12/1964 |
| JP | 42-1186 | 1/1967 |
| JP | 49-44350 | 11/1974 |
| JP | 56-82098 | 7/1981 |
| JP | 63-230094 | 9/1988 |

OTHER PUBLICATIONS

K. W. Harlow, et al., Journal of Bacteriology, vol. 177, No. 8, pp. 2236 to 2240, "Cloning and Characterization of the gsk Gene Encoding Guanosine Kinase of *Escherichia coli*", Apr. 1995.

H. Mori, et al., Journal of Bacteriology, vol. 177, No. 17, pp. 4921 to 4926, "Cloning of a Guanosine–Inosine Kinase Gene of *Escherichia coli* and Characterization of the Purified Gene Product", Sep. 1995.

Y. Usuda, et al., Journal of Bacteriology, vol. 179, No. 22, pp. 6959 to 6964, "Molecular Cloning and Transcriptional Analysis of a Guanosine Kinase Gene of Brevibacterium Acetylicum ATCC 953", Nov. 1997.

Y. Usuda, et al., Biochimica et Biophysica Acta 1341, pp. 200 to 206, "Characterization of Guanosine Kinase from Brevibacterium Acetylicum ATCC 953", 1997.

H. Shirae, et al., Biosciences Information Service, 1 page, XP–002147617, "Purification and Properties of Purine Nucleoside Phosphorylase from Brevibacterium–Acetylicum ATCC 954", 1991.

H. Shirae, et al., Biosciences Information Service, 1 page, XP–002147618, "Enzymatic Production of Ribavirin from Purine Nucleosides by Brevibacterium–Acetylicum ATCC 954", 1988.

Journal of General Microbiology (1989), pp. 1263–1273.

* cited by examiner

*Primary Examiner*—Tekchand Saidha
(74) *Attorney, Agent, or Firm*—Oblon, Spivak, McClelland, Maier & Neustadt, P.C.

(57) ABSTRACT

The present invention relates to a process for producing 5'-inosinic acid or 5'-guanylic acid for use in seasonings or the like from inosine or guanosine or a precursor thereof using an adenosine triphosphate (ATP)-regenerating microorganism containing a DNA encoding a protein that has the activity of forming 5'-inosinic acid or 5'-guanylic acid from inosine or guanosine. Further, the present invention relates to a novel protein having the inosine-guanosine kinase activity, a gene encoding said protein, a recombinant DNA containing said gene, and a microorganism which is transformed with said recombinant DNA.

7 Claims, No Drawings

SEQUENCE LISTING

<160> NUMBER OF SEQ ID NOS: 17

<210> SEQ ID NO 1
<211> LENGTH: 909
<212> TYPE: DNA
<213> ORGANISM: Exiguobacterium acetylicum
<220> FEATURE:
<221> NAME/KEY: CDS
<222> LOCATION: (1)..(909)
<223> OTHER INFORMATION:

<400> SEQUENCE: 1

| atg | aat | aaa | atc | gcg | gta | atc | gga | aaa | gta | ttc | gtc | gac | ata | aaa | gga | 48 |
| Met | Asn | Lys | Ile | Ala | Val | Ile | Gly | Lys | Val | Phe | Val | Asp | Ile | Lys | Gly | |
| 1 | | | | 5 | | | | | 10 | | | | | 15 | | |

| act | tcg | ttc | gct | cct | ttg | cat | aag | gat | gcg | aaa | aac | gta | gga | gac | atc | 96 |
| Thr | Ser | Phe | Ala | Pro | Leu | His | Lys | Asp | Ala | Lys | Asn | Val | Gly | Asp | Ile | |
| | | | | 20 | | | | | 25 | | | | | 30 | | |

| acg | ttt | tca | aat | gga | gga | aca | gga | cgc | aac | gta | gca | caa | aat | cta | gcc | 144 |
| Thr | Phe | Ser | Asn | Gly | Gly | Thr | Gly | Arg | Asn | Val | Ala | Gln | Asn | Leu | Ala | |
| | | | 35 | | | | | 40 | | | | | 45 | | | |

| gtc | ctc | ggg | aat | gaa | gtt | cgc | ttt | atc | tcg | acg | gtt | acg | aat | gat | cag | 192 |
| Val | Leu | Gly | Asn | Glu | Val | Arg | Phe | Ile | Ser | Thr | Val | Thr | Asn | Asp | Gln | |
| | 50 | | | | | 55 | | | | | 60 | | | | | |

| att | ggc | gtg | gga | gtg | ctc | gat | gag | ctg | aaa | tcc | tac | ggt | gcg | aat | gtg | 240 |
| Ile | Gly | Val | Gly | Val | Leu | Asp | Glu | Leu | Lys | Ser | Tyr | Gly | Ala | Asn | Val | |
| 65 | | | | | 70 | | | | | 75 | | | | | 80 | |

| gat | cac | gtc | gaa | atg | tta | gaa | gat | cat | gga | atg | ggt | atg | tgg | cta | gct | 288 |
| Asp | His | Val | Glu | Met | Leu | Glu | Asp | His | Gly | Met | Gly | Met | Trp | Leu | Ala | |
| | | | | 85 | | | | | 90 | | | | | 95 | | |

| gtc | atg | gat | aac | gag | ggt | gac | ttg | caa | aca | tcg | atc | tcg | aaa | caa | ccg | 336 |
| Val | Met | Asp | Asn | Glu | Gly | Asp | Leu | Gln | Thr | Ser | Ile | Ser | Lys | Gln | Pro | |
| | | | | 100 | | | | | 105 | | | | | 110 | | |

| gat | gcc | aag | ttg | ctc | gaa | gag | gcg | att | tta | cgt | caa | tcg | atc | tat | gca | 384 |
| Asp | Ala | Lys | Leu | Leu | Glu | Glu | Ala | Ile | Leu | Arg | Gln | Ser | Ile | Tyr | Ala | |
| | | | 115 | | | | | 120 | | | | | 125 | | | |

| ctc | gat | gga | gtc | gat | gcc | gtt | gca | atc | gat | ttg | gat | ttg | tcc | gtc | acg | 432 |
| Leu | Asp | Gly | Val | Asp | Ala | Val | Ala | Ile | Asp | Leu | Asp | Leu | Ser | Val | Thr | |
| | 130 | | | | | 135 | | | | | 140 | | | | | |

| gtc | tta | gaa | cgt | ttg | att | cat | tta | tgt | cgt | aag | atg | gag | ttg | cca | ttg | 480 |
| Val | Leu | Glu | Arg | Leu | Ile | His | Leu | Cys | Arg | Lys | Met | Glu | Leu | Pro | Leu | |
| 145 | | | | | 150 | | | | | 155 | | | | | 160 | |

| ttt | ggt | gtt | tgt | ggt | cac | ttg | agc | gtc | atc | gaa | cga | aat | cgt | cat | ctg | 528 |
| Phe | Gly | Val | Cys | Gly | His | Leu | Ser | Val | Ile | Glu | Arg | Asn | Arg | His | Leu | |
| | | | | 165 | | | | | 170 | | | | | 175 | | |

| cta | caa | ggg | ttc | act | gga | ttc | att | tgt | agc | cga | gaa | gag | gct | gaa | att | 576 |
| Leu | Gln | Gly | Phe | Thr | Gly | Phe | Ile | Cys | Ser | Arg | Glu | Glu | Ala | Glu | Ile | |
| | | | | 180 | | | | | 185 | | | | | 190 | | |

| ctg | tct | gat | cta | tcg | atc | gtg | acg | gtc | gaa | gat | gcg | att | cat | gta | gca | 624 |
| Leu | Ser | Asp | Leu | Ser | Ile | Val | Thr | Val | Glu | Asp | Ala | Ile | His | Val | Ala | |
| | | | 195 | | | | | 200 | | | | | 205 | | | |

| aat | gag | cta | gcg | aaa | aag | ggc | gct | ccg | ttt | acg | gtc | gtg | acg | atg | agt | 672 |

```
Asn Glu Leu Ala Lys Lys Gly Ala Pro Phe Thr Val Thr Met Ser
    210                 215                 220 gaa ctg ggg gcg gtc tac gtt gat cgt cgt acg gcg aca tca ggt cac        720
Glu Leu Gly Ala Val Tyr Val Asp Arg Arg Thr Ala Thr Ser Gly His
225                 230                 235                 240 gtc gga acg aaa aaa gtg aag gtt gtc gac tca acg gga gca ggc gat        768
Val Gly Thr Lys Lys Val Lys Val Val Asp Ser Thr Gly Ala Gly Asp
                245                 250                 255 tcc ttc ttc tcc gca gtc ttg tcc gaa ttg aca cag gaa aag tca gca        816
Ser Phe Phe Ser Ala Val Leu Ser Glu Leu Thr Gln Glu Lys Ser Ala
            260                 265                 270 gaa gag gct ttg aag ctt ggt atg aag gtc gca gca gaa gtc atc gct        864
Glu Glu Ala Leu Lys Leu Gly Met Lys Val Ala Ala Glu Val Ile Ala
        275                 280                 285 tca aca gag aat gga ctc gtt cct gaa atg cta gat gct ctt caa            909
Ser Thr Glu Asn Gly Leu Val Pro Glu Met Leu Asp Ala Leu Gln
    290                 295                 300

<210> SEQ ID NO 2
<211> LENGTH: 303
<212> TYPE: PRT
<213> ORGANISM: Exiguobacterium acetylicum

<400> SEQUENCE: 2

Met Asn Lys Ile Ala Val Ile Gly Lys Val Phe Val Asp Ile Lys Gly
1               5                   10                  15

Thr Ser Phe Ala Pro Leu His Lys Asp Ala Lys Asn Val Gly Asp Ile
                20                  25                  30

Thr Phe Ser Asn Gly Gly Thr Gly Arg Asn Val Ala Gln Asn Leu Ala
            35                  40                  45

Val Leu Gly Asn Glu Val Arg Phe Ile Ser Thr Val Thr Asn Asp Gln
        50                  55                  60

Ile Gly Val Gly Val Leu Asp Glu Leu Lys Ser Tyr Gly Ala Asn Val
65                  70                  75                  80

Asp His Val Glu Met Leu Glu Asp His Gly Met Gly Met Trp Leu Ala
                85                  90                  95

Val Met Asp Asn Glu Gly Asp Leu Gln Thr Ser Ile Ser Lys Gln Pro
                100                 105                 110

Asp Ala Lys Leu Leu Glu Glu Ala Ile Leu Arg Gln Ser Ile Tyr Ala
            115                 120                 125

Leu Asp Gly Val Asp Ala Val Ala Ile Asp Leu Asp Leu Ser Val Thr
        130                 135                 140

Val Leu Glu Arg Leu Ile His Leu Cys Arg Lys Met Glu Leu Pro Leu
145                 150                 155                 160

Phe Gly Val Cys Gly His Leu Ser Val Ile Glu Arg Asn Arg His Leu
                165                 170                 175

Leu Gln Gly Phe Thr Gly Phe Ile Cys Ser Arg Glu Glu Ala Glu Ile
            180                 185                 190

Leu Ser Asp Leu Ser Ile Val Thr Val Glu Asp Ala Ile His Val Ala
        195                 200                 205

Asn Glu Leu Ala Lys Lys Gly Ala Pro Phe Thr Val Thr Met Ser
210                 215                 220

Glu Leu Gly Ala Val Tyr Val Asp Arg Arg Thr Ala Thr Ser Gly His
225                 230                 235                 240

Val Gly Thr Lys Lys Val Lys Val Val Asp Ser Thr Gly Ala Gly Asp
                245                 250                 255
```

```
Ser Phe Phe Ser Ala Val Leu Ser Glu Leu Thr Gln Glu Lys Ser Ala
            260                 265                 270

Glu Glu Ala Leu Lys Leu Gly Met Lys Val Ala Ala Glu Val Ile Ala
        275                 280                 285

Ser Thr Glu Asn Gly Leu Val Pro Glu Met Leu Asp Ala Leu Gln
    290                 295                 300

<210> SEQ ID NO 3
<211> LENGTH: 28
<212> TYPE: PRT
<213> ORGANISM: Exiguobacterium acetylicum
<220> FEATURE:
<221> NAME/KEY: MISC_FEATURE
<222> LOCATION: (18)..(18)
<223> OTHER INFORMATION: Xaa = unknown amino acid

<400> SEQUENCE: 3

Met Asn Lys Ile Ala Val Ile Gly Lys Val Phe Val Asp Ile Lys Gly
1               5                   10                  15

Thr Xaa Phe Ala Pro Leu His Lys Asp Ala Lys Asn
        20                  25

<210> SEQ ID NO 4
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n = a, c, g, or t

<400> SEQUENCE: 4
atgaayaara thgcngt                                                  17

<210> SEQ ID NO 5
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t

<400> SEQUENCE: 5
ttyttngcrt cyttrtg                                                  17

<210> SEQ ID NO 6
<211> LENGTH: 23
<212> TYPE: DNA
<213> ORGANISM: Artificial Sequence
<220> FEATURE:
<223> OTHER INFORMATION: Synthetic DNA

<400> SEQUENCE: 6
taatcggaaa agtattcgtc gac                                           23

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA
```

<400> SEQUENCE: 7
ggaacttcgt tcgctccttt g　　　　　　　　　　　　　　　　　　　　　　　　21

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
ggctgcagga atgaataaaa tcgcggtaat　　　　　　　　　　　　　　　　　　　　30

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
gggcatgctg gaaagacata atacgtttcg　　　　　　　　　　　　　　　　　　　　30

<210> SEQ ID NO 10
<211> LENGTH: 1302
<212> TYPE: DNA
<213> ORGANISM: Escherichia coli
<220> FEATURE:
<221> NAME/KEY: CDS
<222> LOCATION: (1)..(1053)
<223> OTHER INFORMATION:

<400> SEQUENCE: 10

```
atg aaa ttt ccc ggt aaa cgt aaa tcc aaa cat tac ttc ccc gta aac      48
Met Lys Phe Pro Gly Lys Arg Lys Ser Lys His Tyr Phe Pro Val Asn
1               5                  10                  15 gca cgc gat ccg ctg ctt cag caa ttc cag cca gaa aac gaa acc agc      96
Ala Arg Asp Pro Leu Leu Gln Gln Phe Gln Pro Glu Asn Glu Thr Ser
            20                  25                  30 gct gcc tgg gta gtg ggt atc gat caa acg ctg gtc gat att gaa gcg     144
Ala Ala Trp Val Val Gly Ile Asp Gln Thr Leu Val Asp Ile Glu Ala
        35                  40                  45 aaa gtg gat gat gaa ttt att gag cgt tat gga tta agc gcc ggg cat     192
Lys Val Asp Asp Glu Phe Ile Glu Arg Tyr Gly Leu Ser Ala Gly His
    50                  55                  60 tca ctg gtg att gag gat gat gta gcc gaa gcg ctt tat cag gaa cta     240
Ser Leu Val Ile Glu Asp Asp Val Ala Glu Ala Leu Tyr Gln Glu Leu
65                  70                  75                  80 aaa cag aaa aac ctg att acc cat cag ttt gcg ggt ggc acc att ggt     288
Lys Gln Lys Asn Leu Ile Thr His Gln Phe Ala Gly Gly Thr Ile Gly
                85                  90                  95 aac acc atg cac aac tac tcg gtg ctc gcg gac gac cgt tcg gtg ctg     336
Asn Thr Met His Asn Tyr Ser Val Leu Ala Asp Asp Arg Ser Val Leu
            100                 105                 110 ctg ggc gtc atg tgc agc aat att gaa att ggc agt tat gcc tat cgt     384
Leu Gly Val Met Cys Ser Asn Ile Glu Ile Gly Ser Tyr Ala Tyr Arg
        115                 120                 125 tac ctg tgt aac act tcc agc cgt acc gat ctt aac tat cta caa ggc     432
Tyr Leu Cys Asn Thr Ser Ser Arg Thr Asp Leu Asn Tyr Leu Gln Gly
    130                 135                 140 gtg gat ggc ccg att ggt cgt tgc ttt acg ctg att ggc gag tcc ggg     480
Val Asp Gly Pro Ile Gly Arg Cys Phe Thr Leu Ile Gly Glu Ser Gly
145                 150                 155                 160
```

```
gaa cgt acc ttt gct atc agt cca ggc cac atg aac cag ctg cgg gct      528
Glu Arg Thr Phe Ala Ile Ser Pro Gly His Met Asn Gln Leu Arg Ala
            165                 170                 175 gaa agc att ccg gaa gat gtg att gcc gga gcc tcg gca ctg gtt ctc      576
Glu Ser Ile Pro Glu Asp Val Ile Ala Gly Ala Ser Ala Leu Val Leu
        180                 185                 190 acc tca tat ctg gtg cgt tgc aag ccg ggt gaa ccc atg ccg gaa gca      624
Thr Ser Tyr Leu Val Arg Cys Lys Pro Gly Glu Pro Met Pro Glu Ala
    195                 200                 205 acc atg aaa gcc att gag tac gcg aag aaa tat aac gta ccg gtg gtg      672
Thr Met Lys Ala Ile Glu Tyr Ala Lys Lys Tyr Asn Val Pro Val Val
210                 215                 220 ctg acg ctg ggc acc aag ttt gtc att gcc gag aat ccg cag tgg tgg      720
Leu Thr Leu Gly Thr Lys Phe Val Ile Ala Glu Asn Pro Gln Trp Trp
225                 230                 235                 240 cag caa ttc ctc aaa gat cac gtc tct atc ctt gcg atg aac gaa gat      768
Gln Gln Phe Leu Lys Asp His Val Ser Ile Leu Ala Met Asn Glu Asp
                245                 250                 255 gaa gcc gaa gcg ttg acc gga gaa agc gat ccg ttg ttg gca tct gac      816
Glu Ala Glu Ala Leu Thr Gly Glu Ser Asp Pro Leu Leu Ala Ser Asp
            260                 265                 270 aag gcg ctg gac tgg gta gat ctg gtg ctg tgc acc gcc ggg cca atc      864
Lys Ala Leu Asp Trp Val Asp Leu Val Leu Cys Thr Ala Gly Pro Ile
        275                 280                 285 ggc ttg tat atg gcg ggc ttt acc gaa gac gaa gcg aaa cgt aaa acc      912
Gly Leu Tyr Met Ala Gly Phe Thr Glu Asp Glu Ala Lys Arg Lys Thr
    290                 295                 300 cag cat ccg ctg ctg ccg ggc gct ata gcg gaa ttc aac cag tat gag      960
Gln His Pro Leu Leu Pro Gly Ala Ile Ala Glu Phe Asn Gln Tyr Glu
305                 310                 315                 320 ttt agc cgc gcc atg cgc cac aag gat tgc cag aat ccg ctg cgt gta     1008
Phe Ser Arg Ala Met Arg His Lys Asp Cys Gln Asn Pro Leu Arg Val
                325                 330                 335 tat tcg cac att gcg ccg tac tgg gcg ggc cgg aaa aaa tca tga         1053
Tyr Ser His Ile Ala Pro Tyr Trp Ala Gly Arg Lys Lys Ser
            340                 345                 350 acactaatgg agcgggggat gggcgcattg gcagcgttgc tgcatgacat taccgccaac   1113
agctaccatc gtagcaacgt accaaactcc agcaaacata aattcacctg gttaacttat   1173
tcatcgttag cgcaggtgtg taaatatgct aaccgtgtga gctatcaggt actgaaccag   1233
cattcacctc gtttaacgcg cggcttgccg gagcgtgaag acagcctgga agagtcttac   1293
tgggatcgt                                                           1302

<210> SEQ ID NO 11
<211> LENGTH: 350
<212> TYPE: PRT
<213> ORGANISM: Escherichia coli

<400> SEQUENCE: 11

Met Lys Phe Pro Gly Lys Arg Ser Lys His Tyr Phe Pro Val Asn
1               5                   10                  15

Ala Arg Asp Pro Leu Leu Gln Gln Phe Gln Pro Glu Asn Glu Thr Ser
            20                  25                  30

Ala Ala Trp Val Val Gly Ile Asp Gln Thr Leu Val Asp Ile Glu Ala
        35                  40                  45

Lys Val Asp Asp Glu Phe Ile Glu Arg Tyr Gly Leu Ser Ala Gly His
    50                  55                  60
```

```
Ser Leu Val Ile Glu Asp Val Ala Glu Ala Leu Tyr Gln Glu Leu
 65                  70                  75                  80

Lys Gln Lys Asn Leu Ile Thr His Gln Phe Ala Gly Gly Thr Ile Gly
                 85                  90                  95

Asn Thr Met His Asn Tyr Ser Val Leu Ala Asp Asp Arg Ser Val Leu
            100                 105                 110

Leu Gly Val Met Cys Ser Asn Ile Glu Ile Gly Ser Tyr Ala Tyr Arg
        115                 120                 125

Tyr Leu Cys Asn Thr Ser Ser Arg Thr Asp Leu Asn Tyr Leu Gln Gly
    130                 135                 140

Val Asp Gly Pro Ile Gly Arg Cys Phe Thr Leu Ile Gly Glu Ser Gly
145                 150                 155                 160

Glu Arg Thr Phe Ala Ile Ser Pro Gly His Met Asn Gln Leu Arg Ala
                165                 170                 175

Glu Ser Ile Pro Glu Asp Val Ile Ala Gly Ala Ser Ala Leu Val Leu
            180                 185                 190

Thr Ser Tyr Leu Val Arg Cys Lys Pro Gly Glu Pro Met Pro Glu Ala
        195                 200                 205

Thr Met Lys Ala Ile Glu Tyr Ala Lys Lys Tyr Asn Val Pro Val Val
    210                 215                 220

Leu Thr Leu Gly Thr Lys Phe Val Ile Ala Glu Asn Pro Gln Trp Trp
225                 230                 235                 240

Gln Gln Phe Leu Lys Asp His Val Ser Ile Leu Ala Met Asn Glu Asp
                245                 250                 255

Glu Ala Glu Ala Leu Thr Gly Glu Ser Asp Pro Leu Leu Ala Ser Asp
            260                 265                 270

Lys Ala Leu Asp Trp Val Asp Leu Val Leu Cys Thr Ala Gly Pro Ile
        275                 280                 285

Gly Leu Tyr Met Ala Gly Phe Thr Glu Asp Glu Ala Lys Arg Lys Thr
    290                 295                 300

Gln His Pro Leu Leu Pro Gly Ala Ile Ala Glu Phe Asn Gln Tyr Glu
305                 310                 315                 320

Phe Ser Arg Ala Met Arg His Lys Asp Cys Gln Asn Pro Leu Arg Val
                325                 330                 335

Tyr Ser His Ile Ala Pro Tyr Trp Ala Gly Arg Lys Lys Ser
            340                 345                 350

<210> SEQ ID NO 12
<211> LENGTH: 83
<212> TYPE: PRT
<213> ORGANISM: Escherichia coli

<400> SEQUENCE: 12

Thr Leu Met Glu Arg Gly Met Gly Ala Leu Ala Leu Leu His Asp
 1               5                  10                  15

Ile Thr Ala Asn Ser Tyr His Arg Ser Asn Val Pro Asn Ser Ser Lys
                 20                  25                  30

His Lys Phe Thr Trp Leu Thr Tyr Ser Ser Leu Ala Gln Val Cys Lys
             35                  40                  45

Tyr Ala Asn Arg Val Ser Tyr Gln Val Leu Asn Gln His Ser Pro Arg
    50                  55                  60

Leu Thr Arg Gly Leu Pro Glu Arg Glu Asp Ser Leu Glu Glu Ser Tyr
 65                  70                  75                  80

Trp Asp Arg
```

-continued

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
ggctgcagcc atgaaatttc ccggtaaacg                                           30

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14
ggaagcttaa cgatcccagt aagactcttc                                           30

<210> SEQ ID NO 15
<211> LENGTH: 72
<212> TYPE: DNA
<213> ORGANISM: Artificial Sequence
<220> FEATURE:
<223> OTHER INFORMATION: Synthetic DNA

<400> SEQUENCE: 15
ggggatcctg ttgacaatta atcatcgaac tagttaacag tacgcaagtt cacgtaaaaa          60
gggtctgcag cc                                                              72

<210> SEQ ID NO 16
<211> LENGTH: 924
<212> TYPE: DNA
<213> ORGANISM: Exiguobacterium aurantiacum
<220> FEATURE:
<221> NAME/KEY: CDS
<222> LOCATION: (1)..(924)
<223> OTHER INFORMATION:

<400> SEQUENCE: 16

```
atg aat acg att gca gta atc ggc aaa gtg ttt gtc gac ata aaa gga            48
Met Asn Thr Ile Ala Val Ile Gly Lys Val Phe Val Asp Ile Lys Gly
1               5                   10                  15 acg tcg ttc gcc ccc atc cat aaa gat gcg aaa aac gtc gga gat atc            96
Thr Ser Phe Ala Pro Ile His Lys Asp Ala Lys Asn Val Gly Asp Ile
            20                  25                  30 gcc ttc tca aac ggt ggc acc gga cga aac gtc gct cag aac tta ggt           144
Ala Phe Ser Asn Gly Gly Thr Gly Arg Asn Val Ala Gln Asn Leu Gly
        35                  40                  45 gtc ctc ggt aac gat gtt cgg ttc gtc tcg acc gtg acg aac gat caa           192
Val Leu Gly Asn Asp Val Arg Phe Val Ser Thr Val Thr Asn Asp Gln
    50                  55                  60 atc gga atc ggt gtc ctc gaa gaa cta cgc agt ttg aac gtc aat gtc           240
Ile Gly Ile Gly Val Leu Glu Glu Leu Arg Ser Leu Asn Val Asn Val
65                  70                  75                  80 gaa cac gtc gac ttg ctc gaa gac aac ggc atg ggt atg tgg ctc gcg           288
Glu His Val Asp Leu Leu Glu Asp Asn Gly Met Gly Met Trp Leu Ala
                85                  90                  95 gtc atg gac aat aac ggt gac ctc cag acg tca atc tca aaa caa cct           336
Val Met Asp Asn Asn Gly Asp Leu Gln Thr Ser Ile Ser Lys Gln Pro
            100                 105                 110 gac gag gcg atg atg gaa caa tgc atc ctc cgt cgc atc gat acc gtt           384
```

```
                                                                             -continued Asp Glu Ala Met Met Glu Gln Cys Ile Leu Arg Arg Ile Asp Thr Val
            115                 120                 125 ttc gcc gag agc acg gct gtc gcc atc gac ctc gac tta tcg gtc aac           432
Phe Ala Glu Ser Thr Ala Val Ala Ile Asp Leu Asp Leu Ser Val Asn
130                 135                 140 gtc tta aac gag acg att gaa ttg tgc cgt gag atg aaa ctc ccg cta           480
Val Leu Asn Glu Thr Ile Glu Leu Cys Arg Glu Met Lys Leu Pro Leu
145                 150                 155                 160 tac ggt gta tgt ggt cac ctc tcg gtc atc gaa cgc aac cgt cac ttg           528
Tyr Gly Val Cys Gly His Leu Ser Val Ile Glu Arg Asn Arg His Leu
                165                 170                 175 ctc caa ggg ttc acg ggc ttc atc tgt agc cgc gaa gaa gcc gag att           576
Leu Gln Gly Phe Thr Gly Phe Ile Cys Ser Arg Glu Glu Ala Glu Ile
            180                 185                 190 ctc tcg gat atg tcc atc gtc acg gtt gac gat gcc ctt cgc gtc gcc           624
Leu Ser Asp Met Ser Ile Val Thr Val Asp Asp Ala Leu Arg Val Ala
        195                 200                 205 gag gtg ctc gcc atg aaa gga gcg ccg ctc acg att gtc acg atg agc           672
Glu Val Leu Ala Met Lys Gly Ala Pro Leu Thr Ile Val Thr Met Ser
    210                 215                 220 gag ctc gga gcc gtc tac gtc gac ctt cgc acg aac gaa caa ggt cac           720
Glu Leu Gly Ala Val Tyr Val Asp Leu Arg Thr Asn Glu Gln Gly His
225                 230                 235                 240 gtg ccg acg acg aaa gtg aaa gtt gcc gac tcc aca ggc gcc ggg gat           768
Val Pro Thr Thr Lys Val Lys Val Ala Asp Ser Thr Gly Ala Gly Asp
                245                 250                 255 tcc ttc ttc tct gcc gtt att tcc gag ctc atg aaa gag cat tcg att           816
Ser Phe Phe Ser Ala Val Ile Ser Glu Leu Met Lys Glu His Ser Ile
            260                 265                 270 gaa gat gca ctt cgt ctc ggc atg cgt gtc gcc ggg aaa gtc atc ggc           864
Glu Asp Ala Leu Arg Leu Gly Met Arg Val Ala Gly Lys Val Ile Gly
        275                 280                 285 tct cat gac aac gga ctg acg cct gag atg tat gct tca ctt gaa caa           912
Ser His Asp Asn Gly Leu Thr Pro Glu Met Tyr Ala Ser Leu Glu Gln
    290                 295                 300 cca aca cgt gac                                                           924
Pro Thr Arg Asp
305

<210> SEQ ID NO 17
<211> LENGTH: 308
<212> TYPE: PRT
<213> ORGANISM: Exiguobacterium aurantiacum

<400> SEQUENCE: 17

Met Asn Thr Ile Ala Val Ile Gly Lys Val Phe Val Asp Ile Lys Gly
1               5                   10                  15

Thr Ser Phe Ala Pro Ile His Lys Asp Ala Lys Asn Val Gly Asp Ile
            20                  25                  30

Ala Phe Ser Asn Gly Gly Thr Gly Arg Asn Val Ala Gln Asn Leu Gly
        35                  40                  45

Val Leu Gly Asn Asp Val Arg Phe Val Ser Thr Val Thr Asn Asp Gln
    50                  55                  60

Ile Gly Ile Gly Val Leu Glu Glu Leu Arg Ser Leu Asn Val Asn Val
65                  70                  75                  80

Glu His Val Asp Leu Leu Glu Asp Asn Gly Met Gly Met Trp Leu Ala
                85                  90                  95

Val Met Asp Asn Asn Gly Asp Leu Gln Thr Ser Ile Ser Lys Gln Pro
            100                 105                 110
```

-continued

```
Asp Glu Ala Met Met Glu Gln Cys Ile Leu Arg Arg Ile Asp Thr Val
            115                 120                 125

Phe Ala Glu Ser Thr Ala Val Ala Ile Asp Leu Asp Leu Ser Val Asn
            130                 135                 140

Val Leu Asn Glu Thr Ile Glu Leu Cys Arg Glu Met Lys Leu Pro Leu
145                 150                 155                 160

Tyr Gly Val Cys Gly His Leu Ser Val Ile Glu Arg Asn Arg His Leu
                165                 170                 175

Leu Gln Gly Phe Thr Gly Phe Ile Cys Ser Arg Glu Glu Ala Glu Ile
            180                 185                 190

Leu Ser Asp Met Ser Ile Val Thr Val Asp Asp Ala Leu Arg Val Ala
            195                 200                 205

Glu Val Leu Ala Met Lys Gly Ala Pro Leu Thr Ile Val Thr Met Ser
    210                 215                 220

Glu Leu Gly Ala Val Tyr Val Asp Leu Arg Thr Asn Glu Gln Gly His
225                 230                 235                 240

Val Pro Thr Thr Lys Val Lys Val Ala Asp Ser Thr Gly Ala Gly Asp
                245                 250                 255

Ser Phe Phe Ser Ala Val Ile Ser Glu Leu Met Lys Glu His Ser Ile
                260                 265                 270

Glu Asp Ala Leu Arg Leu Gly Met Arg Val Ala Gly Lys Val Ile Gly
            275                 280                 285

Ser His Asp Asn Gly Leu Thr Pro Glu Met Tyr Ala Ser Leu Glu Gln
    290                 295                 300

Pro Thr Arg Asp
305
```

PROCESS FOR PRODUCING NUCLEIC ACIDS

TECHNICAL FIELD

The present invention relates to a process for producing 5'-inosinic acid or 5'-guanylic acid for use in seasonings or the like from inosine or guanosine or a precursor thereof using adenosine triphosphate (ATP)-producing microorganisms containing a DNA encoding a protein that has the activity of forming 5'-inosinic acid or 5'-guanylic acid from inosine or guanosine.

Further, the present invention relates to a novel protein having the inosine-guanosine kinase activity, a gene encoding said protein, a recombinant DNA containing said gene, and a microorganism which is transformed with said recombinant DNA.

BACKGROUND ART

In order to produce 5'-inosinic acid by phosphorylating inosine using microorganisms, a method using p-nitrophenyl phosphate (Japanese Patent Publication No. 29,858/1964), a method using inorganic phosphoric acids (Japanese Patent Publication Nos. 1,186/1967 and 44,350/1974), a method using acetyl phosphate (Japanese Patent Application Laid-Open No. 82,098/1981), and a method using ATP (Japanese Patent Application Laid-Open No. 230,094/1988) have been developed so far. However, the accumulation of 5'-inosinic acid which is produced by these methods has not necessarily been satisfactory. As an improved method of phosphorylating inosine with ATP, a method which comprises obtaining a gene encoding inosine-guanosine kinase of *Escherichia coli*, preparing an *E. coli* strain having the increased inosine-guanosine kinase activity by recombinant DNA technique, and phosphorylating inosine or guanosine using this strain to produce 5'-inosinic acid or 5'-guanylic acid, has been also developed (WO 91/08286). However, this method requires that a microorganism for regenerating ATP to be consumed in the reaction is separately cultured and that its cells are added to the reaction solution. Accordingly, a method of obtaining 5'-inosinic acid or 5'-guanylic acid more efficiently has been in demand.

Moreover, it is only known that the inosine-guanosine kinase gene is presents in some microorganisms such as *E. coli* [J. Gen. Microbiol., 135, 1263–1273 (1989)].

The present inventors have developed a process for producing 5'-inosinic acid and/or 5'-guanylic acid more efficiently. Consequently, they have found that 5'-inosinic acid and/or 5'-guanylic acid can be produced easily in a high yield by introducing a gene encoding an inosine-guanosine kinase into a microorganism having sufficient ability to regenerate ATP to be consumed in the reaction. They have also found a novel inosine-guanosine kinase having an amino-acid sequence which is different from that of an inosine-guanosine kinase derived from *E. coli*.

DISCLOSURE OF THE INVENTION

The present invention relates to a process for producing 5'-inosinic acid or 5'-guanylic acid for use in seasonings or the like from inosine or guanosine or a precursor thereof easily in a high yield. More specifically, the present invention is to provide a process in which a gene encoding a protein that has the activity of converting inosine and/or guanosine into 5'-inosinic acid and/or 5'-guanylic acid is introduced into a microorganism having a sufficient ability to regenerate ATP to be consumed in the reaction, whereby 5'-inosinic acid and/or 5'-guanylic acid is easily obtained efficiently in a high yield in the presence of only the microorganism having the gene introduced therein without separately culturing another microorganism for regenerating ATP to be consumed in the reaction and adding it to the reaction solution.

Further, the present invention is to provide a novel protein which can be obtained from microorganisms belonging to *Exiguobacterium acetylicum* and which has the activity of converting inosine and guanosine into 5'-inosinic acid and 5'-guanylic acid, respectively, a gene encoding said protein, a recombinant DNA containing said gene, a microorganism which is transformed with said recombinant DNA, and a process for producing 5'-inosinic acid and/or 5'-guanylic acid using this microorganism.

The protein of the present invention is novel in that the amino-acid sequence of the protein of the present invention is vastly different from that of a known protein having inosine-guanosine kinase activity. An inosine-guanosine kinase derived from *E.coli* has been already known. The present inventors have found that a protein having the inosine-guanosine kinase activity is also produced in microorganisms belonging to the genus Exiguobacterium which were not known before to have the inosine-guanosine kinase activity, and they have succeeded in isolating this protein and cloning the gene encoding the protein. This protein is much different from the known protein with respect to the amino-acid sequence.

It has been found for the first time by the present inventors that the protein having the amino-acid sequence quite different from that of the known protein having the inosine-guanosine activity has the same activity as the known protein.

That is, the present invention relates to the following:

(1) a process for producing 5'-inosinic acid or 5'-guanylic acid, which comprises contacting a transformant obtained by introducing a gene encoding a protein having inosine-guanosine kinase activity into a microorganism capable of reproducing ATP, with inosine or guanosine or a precursor thereof, an energy source and a phosphate donor, accumulating 5'-inosinic acid or 5'-guanylic arid in the reaction solution, and collecting the same therefrom, (2) a process for producing 5'-inosinic acid or 5'-guanylic acid according to (1), wherein the microorganism capable of reproducing ATP belongs to a genus selected from the group consisting of *Corynebacterium, Escherichia, Saccharomyces, Staphylococcus* and *Candida,*

(3) a process for producing 5'-inosinic acid or 5'-guanylic acid according to (1), wherein the microorganism capable of reproducing ATP belongs to *Corynebacterium ammoniagenes,*

(4) a process for producing 5'-inosinic acid or 5'-guanylic acid according to any one of (1) to (3), wherein the gene encoding the protein having inosine-guanosine kinase activity is a gene derived from *Exiguobacterium acetylicum* or a gene capable of hybridizing said gene, (5) a process for producing 5'-inosinic acid or 5'-guanylic acid according to any one of (1) to (3), wherein the gene encoding the protein having inosine-guanosine kinase activity is a gene derived from Escherichia coli or a gene capable of hybridizing said gene, (6) a transformant obtained by introducing a gene encoding a protein having inosine-guanosine kinase activity into a microorganism capable of reproducing ATP, (7) a transformant according (6), wherein the microorganism capable of reproducing ATP belongs to a genus selected from the group consisting of *Corynebacterium, Escherichia, Saccharomyces, Staphylococcus* and *Candida*, (8) a transformant according to (6), wherein the microorganism, capable of reproducing ATP belongs to *Corynebacterium ammoniagenes*, (9) a transformant according to any of claims 6 to 8, wherein the gene encoding a protein having inosine-guanosine kinase activity is a gene derived from *Exiguobacterium acetylicum* or a gene capable of hybridizing said gene,

(10) a transformant according to any of (6) to (8), wherein the gene encoding a protein having inosine-guanosine kinase activity is a gene derived from *Escherichia coli* or a gene capable of hybridizing said gene,

(11) a recombinant DNA being capable of replicating in *Corynebacterium ammoniagenes* and containing a gene encoding a protein having inosine-guanosine kinase activity,

(12) a recombinant DNA according to (11), wherein the gene encoding a protein having inosine-guanosine kinase activity is a gene derived from *Exiguobacterium acetylicum* or a gene capable of hybridizing said gene,

(13) a recombinant DNA according to (11), wherein the gene encoding a protein having inosine-guanosine kinase activity is a gene derived from *Escherichia coli* or a gene capable of hybridizing said gene,

(14) a protein obtainable from a microorganism belonging to *Exiguobacterium acetylicum* having inosine-guanosine kinase activity and the following characteristics:

1. Action

The enzyme transfers a phosphate group to a nucleoside in the presence of a phosphate donor and forms a nucleoside 5'-monophosphate.

2. Substrate Specificity

A phosphate group in the Y-position of a nucleoside triphosphate is transferred to the other nucleoside.

3. Optimum pH pH 7.7–9.9.

4. pH Stability pH 6.7–12.1.

5. Optimum Temperature

30–50° C.

6. Metal Requirement

Magnesium ion, manganese ion, cobalt ion or iron ion

7. Influence of Metal Ions

The activity of the enzyme is strongly inhibited by copper ion and mercury ion, and is also inhibited by zinc ion and cadmium ion.

8. Km Values

Km value is 0.03 mM for guanosine, 1 mM for inosine, and 1.6 mM for ATP when guanosine is used as a substrate.

9. Molecular Weight

The enzyme has a molecular weight of approximately 36 kilodaltons as measured by SDS-polyacrylamide gel electrophoresis.

(15) a protein having inosine-guanosine kinase activity and having the amino acid sequence which is shown in SEQ ID NO:2 or in which a part of amino acids are deleted, substituted or added in the amino acid sequence shown in SEQ ID NO:2,

(16) a gene encoding a protein according to (14) or (15), and

(17) a gene encoding a protein having inosine-guanosine activity, and having a nucleotide sequence shown in SEQ ID NO:1 or being capable of hybridizing a gene having said nucleotide sequence.

In the present specification, the activity of phosphorylating inosine and guanosine with ATP and forming 5'-inosinic acid and 5'-guanylic acid, respectively, is referred to as "inosine-guanosine kinase activity". The protein having this activity is referred to as "an inosine-guanosine kinase". The microorganism having sufficient ability to regenerate ATP to be consumed in the reaction is referred to as "an ATP-producing strain".

The present invention will be described in more detail below.

The inosine-guanosine kinase referred to in the present invention is an enzyme that catalyzes the reaction of phosphorylating inosine and guanosine with ATP or the like to form 5'-inosinic acid and 5'-guanylic acid, respectively. The origin of this enzyme is not particularly limited but inosine-guanosine kinase derived from a microorganism is preferred. It includes not only a novel enzyme obtained from a microorganism belonging to *Exiguobacterium acetylicum* or the like but also a known inosine-guanosine kinase obtained from *E. coli*.

The novel protein which can be obtained from a microorganism belonging to *Exiguobacterium acetylicum* or the like and which has the inosine-guanosine kinase activity can be obtained by culturing the microorganism, disrupting the obtained cells to prepare a crude enzyme extract, and purifying the enzyme from the crude enzyme extract. As an example of such microorganisms, *Exiguobacterium acetylicum* ATCC 953 can be mentioned.

Taxonomically, *Exiguobacterium acetylicum* had been called Brevibacterium acetylicum [Bergey's Manual of Systematic Bacteriology, pp. 1301–1313 (1986)]. However, as a result of the genetic analysis, it is proposed that *Brevibacterium acetylicum* should be transferred to the genus Exiguobacterium as *Exiguobacterium acetylicum* [Int. J. Syst. Bacteriol., 44, 74–82 (1994)].

The inosine-guanosine kinase can be purified by any method that does not impair the inosine-guanosine kinase activity. The purification is generally performed through liquid column chromatography. Specifically, ion-exchange column chromatography using a potassium chloride concentration gradient, hydrophobic column chromatography using an ammonium sulfate concentration gradient, and adsorption column chromatography using a phosphate buffer concentration gradient may be used in combination.

In the present invention, the enzyme which can be obtained from the microorganism belonging to *Exiguobacterium acetylicum* and which has the inosine-guanosine kinase activity has the following properties.

1. Action

The enzyme transfers a phosphate group to a nucleoside in the presence of a phosphate donor and forms a nucleoside 5'-monophosphate.

The phosphate donor is a nucleoside triphosphate. Examples of the nucleoside triphosphate include ATP, 2'-deoxyadenosine triphosphate, guanosine triphosphate, 2'-deoxyguanosine triphosphate, and thymidine triphosphate.

Examples of the nucleoside to which the phosphate group is transferred include inosine, guanosine, and $2^1$-deoxyguanosine.

The nucleoside 5'-monophosphate includes 5'-monophosphate esters of the above-mentioned nucleosides, and 5'-inosinate, 5'-guanylate, 2'-deoxy-5'-guanylate, etc. are given as the examples.

2. Substrate Specificity

A phosphate group in the y-position of the nucleoside triphosphate is transferred to the other nucleoside.

Examples of the nucleoside triphosphate include ATP, 2'-deoxyadenosine triphosphate, guanosine triphosphate, 2'-deoxyguanosine triphosphate, and thymidine triphosphate.

Examples of the other nucleoside to which the phosphate group is transferred include inosine, guanosine, and 2'-deoxyguanosine.

3. Optimum pH

The optimum pH is between 7.7 and 9.9.

4. pH Stability

The activity is stable in the pH range between 6.7 and 12.1.

5. Optimum Temperature

The optimum temperature is between 30 and 50° C.

6. Temperature Stability

The enzyme is inactivated at 40° C. or higher.

7. Metal Requirement

Metal ions are required to proceed with the reaction. The reaction proceeds in the presence of magnesium ion, manganese ion, cobalt ion or iron ion.

8. Influence of Metal Ions

The activity of the enzyme is strongly inhibited by copper ion and mercury ion, and is also inhibited by zinc ion and cadmium ion.

9. Km Value

Km value is 0.03 mM for guanosine, 1 mM for inosine, and 1.6 mM for ATP when guanosine is used as a substrate.

10. Molecular Weight

The enzyme has a molecular weight of approximately 36 kilodaltons as measured by SDS-polyacrylamide gel electrophoresis.

A DNA fragment containing the structural gene encoding the protein that has inosine-guanosine kinase activity can be obtained by a known method using a purified protein. Examples of the known method include a method in which an antibody against the above-mentioned protein is prepared and a chromosomal gene expression library is screened, and a method in which the amino-acid sequence of the protein purified is analyzed and the gene library is screened using a probe which is synthesized based on this amino acid sequence. As the amino acid sequence, an internal amino acid sequence of the protein determined from a polypeptide generated by an appropriate proteinase digestion of the protein, in addition to N-terminal amino acid sequence of the protein. Examples of the probe include oligonucleotides synthesized based on the N-terminal amino-acid sequence or the internal amino-acid sequence, those obtained by amplifying a region corresponding to the N-terminal amino-acid sequence or the internal amino-acid sequence through the polymerase chain reaction (PCR) using a oligonucleotide synthesized based on the sequence, and those obtained by amplifying the region corresponding to a portion from N-terminal to the internal amino acid using oligonucleotides synthesized based on the N-terminal amino-acid sequence and the internal amino-acid sequence as primers. Further, there is a method in which a chromosome is ligated with a double-stranded oligonucleotide which is called a cassette, and the desired fragment is obtained by PCR using a primer of an oligonucleotide formed according to the N-terminal amino-acid sequence and a primer formed according to the sequence of the cassette [Molecular and Cellular Probes, 6, 467 (1992)].

Specifically, a gene encoding a protein that has the inosine-guanine kinase activity of *Exiguobacterium acetylicum* can be obtained by amplifying a DNA fragment corresponding to the N-terminal region using PCR, synthesizing a primer based on the DNA fragment, and amplifying the fragment using PCR with the cassette.

The determined sequence of 28 amino acids in the N-terminal of the protein obtained from *Exiguobacterium acetylicum* ATCC 953 is represented by SEQ ID NO:3 in Sequence Listing. The 18th amino acid was not identified.

Judging form this N-terminal amino acid sequence, the protein of *Exiguobacterium acetylicum* is quite different from the known inosine-guanosine kinase derived from *E. coli* as described in WO 91/08286.

In order to obtain the aimed gene, the DNA encoding the N-terminal portion of the protein having the inosine-guanosine kinase activity is specifically amplified by PCR using the primer synthesized based on the above-mentioned N-terminal amino-acid sequence and using the chromosome of the microorganism belonging to *Exiguobacterium acetylicum* as a template, and is cloned. Ordinarily used is a primer in which the base composition is random, the G+C content is approximately 50%, no specific secondary structure is formed, the chains are not complementary to each other and the length is from 16 to 30 bases. The sequences of the primers are located at both terminals of the nucleotide sequence corresponding to the N-terminal region of the protein and are shown in SEQ ID No: 4 and 5 in Sequence Listing.

In SEQ ID No:4, the 6th nucleotide is a mixture of T and C, 9th nucleotide is a mixture of A and G, 12th nucleotide is a mixture of T, C and A, 15th nucleotide is a mixture of T, C, A and G. And in SEQ ID No:5, the 3rd and 12th nucleotides are a mixture of T and C, 6th nucleotide is a mixture of T, C, A and G, 9th and 15th nucleotides are a mixture of A and G.

Then, the chromosome of the microorganism belonging to *Exiguobacterium acetylicum* is cleaved with an appropriate restriction endonuclease. This cleaved substance is ligated with the cassette to form a template. A DNA fragment containing a structural gene portion or the upstream region of the protein having the inosine-guanosine kinase activity is specifically amplified by PCR using the above-mentioned template and the primer synthesized according to the nucleotide sequence corresponding to the N-terminal amino-acid sequence and the primer synthesized according to the cassette, and is cloned. The primer that satisfies the above-mentioned conditions, as shown in SEQ ID NO:6 and 7 in Sequence Listing, can be used.

A vector which is autonomously replicable in *E. coli* used as a host can be employed as a vector for cloning the gene. Examples of the vector include pUC19, pHSG298, pHSG398 and pBR322. Any strain which is suitable for the replication of the vector can be used as a recipient strain of the resulting recombinant DNA. Examples of the recipient strain include *E. coli* strains such as HB101, JM109 and DH5.

The nucleotide sequence of the inosine-guanosine kinase gene present in thee DNA fragment inserted into the vector and the amino-acid sequence of the protein encoded by this gene can be determined by analyzing the nucleotide sequence of this DNA fragment. The nucleotide sequence and the amino-acid sequence of the inosine-guanosine kinase of *Exiguobacterium acetylicum* ATCC 953 are represented by SEQ ID NO:1 and 2 in Sequence Listing, respectively.

The protein of the present invention comprises 303 amino acids, and the molecular weight is approximately 32.5 kilodaltons.

The protein of the present invention includes not only the protein represented by SEQ ID NO:2 in Sequence Listing but also proteins obtained from other strains belonging to *Exiguobacterium acetylicum* and other natural mutants that have the inosine-guanosine kinase activity.

Further, it is clear for a skilled person that proteins in which a part of the amino-acid sequence is substituted or deleted, proteins in which amino acids are added thereto and partially modified proteins may be used so far as these proteins have the inosine-guanosine kinase activity.

Instead of the gene derived from *Exiguobacterium acetylicum*, a gene which is capable of hybridizing the gene can be used so far as it encodes the inosine-guanosine kinase.

The gene which is capable of hybridizing the gene derived from *Exiguobacterium acetylicum* can be obtained from the following strains.

*Exiguobacterium aurantiacum* ATCC 35652
*Kurthia gibsonii* ATCC 43195
*Kurthia zopfii* JCM 6101.

The gene, as mentioned above can be obtained by a known method using the homology. Specifically, the following method can be employed.

First, the chromosomal DNA of any of the above-mentioned microorganisms is cleaved with an appropriate restriction endonuclease, and the cleaved fragments are subjected to agarose gel electrophoresis. The cleaved fragments are blotted on an appropriate transfer filter. The homologous fragments are detected by the Southern hybridization using the inosine-guanosine kinase gene derived from *Exiguobacterium acetylicum* as the probe to determine the length.

Among the fragments cleaved with the restriction endonuclease, the fragments having the aimed length is purified. The purification is generally conducted through sucrose density gradient centrifugation or recovery from an agarose gel with a glass powder. The thus-purified fragments are ligated with an appropriate vector, and an *E. coli* strain is transformed with the thus-obtained recombinant vector. The clone containing the aimed fragment having the inosine-guanosine kinase gene can be selected from among the resulting transformants using the colony hybridization method.

In the present invention, a gene encoding a known inosine-guanosine kinase can be used instead of the above-mentioned gene encoding the novel-inosine-guanosine kinase.

As the known inosine-guanosine kinase gene, the gene derived from *E. coli* can be used [J. Gen. Microbiol., 135, 1263–1273 (1989); J. Bacteriol. 177, 2236–2240 (1995)], and it can be obtained from, for example, *E. coli* ATCC 27325.

The known gene encoding the inosine-guanosine kinase can be obtained using a known method. The gene encoding the inosine-guanosine kinase which can be used in the present invention can be also obtained from a chromosomal DNA of *E. coli* ATCC 27325 using the following method.

First, primers are synthesized according to the sequence of the inosine-guanosine kinase gene derived from *E. coli* as represented by SEQ ID No:10 in Sequence Listing (WO 91/08286). Ordinarily used are primers in which the base composition is random, the G+C content is approximately 50%, no specific secondary structure is formed, the chains are not complementary to each other and the length is from 15 to 30 bases. The sequences of the primers are located at both terminals of the inosine-guanosine kinase structural gene as shown in SEQ ID Nos. 13 and 14.

Then, the inosine-guanosine kinase structural gene can be amplified from the chromosomal DNA of *E. coli* by PCR using these primers and cloned. A vector derived from *E. coli*, such as pUC19 and pBR322 is used. Any recipient strain which is suitable for the replication of the vector may be used for the resulting recombinant DNA. Examples of this recipient strain include *E. coli* strains such as HB101, JM109 and DH5. In this manner, the recombinant vector having the insertion of the DNA fragment containing the inosine-guanosine kinase gene of *E. coli* is obtained.

A gene which is homologous to the above-mentioned gene derived from *E. coli* and is capable of hybridizing the gene can be used, as in *Exiguobacterium acetylicum*, so far as it encodes the inosine-guanosine kinase.

The thus-obtained DNA fragment containing the gene encoding the protein that has the inosine-guanosine kinase activity is introduced into a host cell which can regenerate ATP after recombining it again with the other suitable vector or inserting the replication origin.

A microorganism which has the sufficient ability to regenerate ATP to be consumed in the reaction from an ATP precursor (ATP-producing ability) is used as the host cell.

In the present invention, the microorganism having the ATP-producing ability may be any microorganism having the ability to regenerate ATP to be consumed in the reaction of converting inosine and/or guanosine into 5'-inosinic acid and/or 5'-guanylic acid from the ATP precursor in the reaction system whereby the reaction can proceed. Examples of this microorganism include microorganisms belonging to the genus *Corynebacterium*, *Escherichia*, *Staphylococcus*, *Saccharomyces* or *Candida*. The microorganisms belonging to *Corynebacterium ammoniagenes* which have a high ability to produce ATP are especially preferable. Incidentally, *Corynebacterium ammoniagenes* was classified before as *Brevibacterium ammoniagenes*.

Specific examples of the microorganisms having the ATP-producing ability which are used in the present invention are strains shown below and mutants derived therefrom.

*Corynebacterium ammoniagenes* (former name: *Brevibacterium ammoniagenes*) ATCC 6872
*Corynebacterium ammoniagenes* (former name: *Brevibacterium ammoniagenes*) ATCC 21295
*Corynebacterium ammoniagenes* (former name: *Brevibacterium ammoniagenes*) ATCC 21477
*Corynebacterium glutamicum* ATCC 13020
*Corynebacterium glutamicum* (former name: *Brevibacterium flavum*) ATCC 14067
*Corynebacterium glutamicum* (former name: *Brevibacterium lactofermentum*) ATCC 13869
*Escherichia coli* B (ATCC 11303)
*Saccharomyces cerevisiae* ATCC 20018
*Staphylococcus aureus* ATCC 4012
*Candida zeylanoides* ATCC 20356
*Candida psychrophila* (former name: *Torulopsis psychrophila*) ATCC 22163

Further, the microorganisms having the ATP-producing activity wherein the degrading activity of inosine and/or guanosine is weak or deficient are preferable. The following microorganisms are taken up from among the above-mentioned microorganisms.

*Corynebacterium ammoniagenes* ATCC 21295
*Corynebacterium ammoniagenes* ATCC 21477

As the ATP-producing microorganisms in the present invention, strains having the ability to produce inosine or guanosine from the precursor of inosine or guanosine in addition to the ATP-producing ability can be also used. In this case, 5'-inosinic acid or 5'-guanylic acid can be produced from the inosine or guanosine precursor instead of inosine or guanosine. Examples of this precursor include saccharides such as glucose, sucrose, molasses and starch hydrolysate, organic acids such as acetic acid, and alcohols such as glycerol and ethanol.

The ATP-producing strains having the ability to produce inosine or guanosine include:

Corynebacterium ammoniagenes ATCC 21478
Corynebacterium ammoniagenes ATCC 21479
Corynebacterium ammoniagenes ATCC 21480

The vector into which the gene encoding the inosine-guanosine kinase is integrated is not particularly limited so long as it can be replicated in the ATP-producing strains which are the recipient strains. For example, when bacteria belonging to the genus Corynebacterium are used as the ATP-producing strains, plasmids which can be autonomously replicated in these bacteria are mentioned. Specific examples thereof include pAM330 (Japanese Patent Application Laid-Open No. 67,699/1983), pHM1519 (Japanese Patent Application Laid-Open No. 77,895/1983), pAJ655, pAJ611, pAJ1844 (Japanese Patent Application Laid-Open No. 192,900/1983), pCG1 (Japanese Patent Application Laid-Open No. 134,500/1982), pCG2 (Japanese Patent Application Laid-Open No. 35,197/1983), pCG4, pCG11 (Japanese Patent Application Laid-Open No. 183,799/1982), pGA1 [Gene, 107, 69 (1991)], pHK4, and pHC4 (Japanese Patent Application Laid-Open No. 7,491/1993). When Escherichia coli is used as the ATP-producing strain, for example, ColE1 plasmid, P15A plasmid, R-factor plasmid, F-factor plasmid and a phage plasmid can be used. Specific examples thereof include pBR322 [Gene, 2, 95 (1977)], pUC19 [Gene, 33, 103 (1985)], pACYC184 [J. Bacteriol, 134, 1141 (1978)], and pSC101 [Proc. Natl. Acad. Sci., U.S.A., 70, 3240 (1973)]. When Saccharomyces cerevisiae is used as the ATP-producing strain, YEp plasmid, YCp plasmid, YRp plasmid and YLp plasmid can be used. Specific examples thereof include YEp24, YRp7 and YCp5b. When Staphylococcus aureus is used as the ATP-producing strain, pRIT5 [EMBO J., 4, 1075 (1985)] can be used.

In order to express the gene encoding the inosine-guanosine kinase at high frequency, it is advisable that the promoter sequence and the SD sequence be located upstream of the gene encoding the inosine-guanosine kinase. A method of introducing these sequences is not particularly limited. The promoter sequence and the SD sequence can be introduced by a method in which the above-mentioned gene is inserted downstream of these sequences using the vector having these sequences, or a method in which these sequences are synthesized and inserted upstream of the above-mentioned gene; The promoter sequence and the SD sequence are not particularly limited. When the bacteria of the genus Corynebacterium are used as the ATP-producing strains, tac, lac and trp promoters derived from E. coli, trp promoter derived from bacteria of the genus Corynebacterium [Gene, 53, 191 (1987) ], fda promoter [Mol. Microbiol., 3, 1625 (1989)] . ppc promoter [Gene, 77, 237 (1989)], lysC promoter (Mol. Microbiol., 5, 1197 (1991) ], gdh promoter [Mol. Microbiol., 6, 317 (1992)], and csp1 and csp2 promoters (Japanese Patent Application Laid-Open 502,548/1994) can be mentioned. When Escherichia coli is used as the ATP-producing strain, tac, lac and trp promoters derived from E. coli, and $P_L$ promoter of λ phage can be mentioned. When Saccharomyces cerevisiae is used as the ATP-producing strain, ADH1, ENO1, PGK1, GAP-DH, GAL1, GAL10, GAL7, PH05 and MFα1 promoters can be mentioned. When Staphylococcus aureus is used as the ATP-producing strain, spa promoter [J. Bacteriol., 159, 713 (1984)] can be mentioned.

A method of introducing into the ATP-producing microorganism the recombinant DNA containing the gene encoding the protein that has the activity of converting inosine and/or guanosine into 5'-inosinic acid and/or 5'-guanylic acid is not particularly limited. This introduction can be performed by a usual method. For example, when the bacteria of the genus Corynebacterium are used as the ATP-producing strain, the protoplast method (Japanese Patent Application Laid-Open No. 183,799/1982) and electroporation (Japanese Patent Application Laid-Open No. 207,791/1990) are especially effective. When Escherichia coli is used as the ATP-producing strain, the calcium chloride method [J. Mol. Biol., 53, 159 (1970)], the method of Hanahan [J. Mol. Biol., 166, 557 (1983)], the SEM method (Gene, 96, 23 (1990)], the method of Chung et al. [Proc. Natl. Acad. Sci., U.S.A., 86, 2172 (1989)], and electroporation [Nucleic Acids Res., 16, 6127 (1988)] can be used. There is a method in which a DNA is introduced by preparing competent cells from cells at the stage of proliferation as reported with respect to Bacillus subtilis [Gene, 1, 153 (1977)). Alternatively, a method in which cells of a DNA recipient strain are formed into protoplasts or spheroplasts that easily incorporate a recombinant DNA and the recombinant DNA is introduced into this DNA recipient strain, as reported with respect to Bacillus subtilis, actinomycetes, and yeasts [Molec. Gen. Genet., 1, 111 (1979), Nature, 274, 398 (1978), and Proc. Natl. Acad. Sci. USA, 75, 1929 (1978)] can be also used. When Saccharomyces cerevisiae is used as the ATP-producing strain, the recombinant DNA can be introduced by the spheroplast method [Proc. Natl. Acad. Sci., U.S.A., 75, 1929 (1978)], the lithium acetate method [J. Bacteriol., 153, 163 (1983)], or electroporation ["Methods in Enzymology", 194, 182 (1991)]. When Staphylococcus aureus is used as the ATP-producing strain, the introduction of the recombinant DNA can be conducted by the protoplast method [Plasmid, 5, 292 (1981)] In the protoplast method, the high frequency can be obtained by the above-mentioned method which is used in Bacillus subtilis. However, as disclosed in Japanese Patent Application Laid-Open No. 183,799/1982, a method in which a DNA is incorporated into a state where protoplasts of cells of bacteria belonging to the genus Corynebacterium are brought into contact with either polyethylene glycol or polyvinyl alcohol and divalent metal ions can be also utilized. The uptake of the DNA can be enhanced by the addition of carboxymethyl cellulose, dextran, Ficol or Pluronic (made by Serva Co.) or the like instead of polyethylene glycol or polyvinyl alcohol.

The recombinant DNA can be introduced into the recipient strain by the electroporation method (refer to Japanese Patent Application Laid-Open No. 207,791/1990). The transformation method used in Examples of the present invention is electroporation.

Further, the inosine-guanosine kinase gene can be integrated into the chromosomal DNA of the ATP-producing microorganisms. The method of integrating this gene into the chromosomal DNA is not particularly limited. For example, a temperature-sensitive replication origin derived from bacteria of the genus Corynebacterium, an inosine-guanosine kinase gene and a marker which gives resistance to antibiotics such as chloramphenicol are inserted into a plasmid vector to form a recombinant DNA. The bacterium of the genus Corynebacterium is transformed with this recombinant DNA. The transformant is cultured in a medium containing antibiotics at a temperature at which the temperature-sensitive replication origin does not function, to form a transformant strain in which the recombinant DNA has been integrated into the chromosomal DNA [J. Bacteriol., 162, 1196 (1985), and Japanese Patent Application Laid-Open No. 7,491/1993]. Or a method using a movable genetic element derived from bacteria of the genus Corynebacterium can be also used ["Mobile Genetic Elements", Academic Press, New York (1983), and WO 93/18151].

The inosine-guanosine kinase activity can be expressed at high level by culturing the thus-obtained transformant of the present invention into which the recombinant DNA containing the gene encoding the protein which has the inosine-guanosine kinase activity has been introduced, in an ordinary culture medium containing a carbon source, a nitrogen source, inorganic salts and optionally trace organic nutrients.

Examples of the carbon source include saccharides such as glucose, sucrose, molasses and starch hydrolysate; organic acids such as acetic acid and citric acid; and alcohols such as ethanol. Examples of the nitrogen source include urea, ammonium salts; aqueous ammonia and ammonia gas. Examples of the inorganic salts include phosphates, and potassium, magnesium, iron and manganese salts. Examples of the trace organic nutrients include amino acids, vitamins, fatty acids and nucleic acids as well as peptone, yeast extract and soybean protein hydrolysate containing any of these.

The cultivation is aerobically carried out at a temperature of from 25 to 37° C. for 10 to 40 hours while adjusting pH between 5 and 9.

After the completion of the cultivation, the activity of the inosine-guanosine kinase accumulated in the culture is measured to confirm the titer. The activity can be measured by the method described in Molec. Gen. Genet. 143, 85–91 (1975) using a substance obtained by disrupting the cells recovered from the culture through centrifugation or the like using sonication or French-press treatment, centrifuging the disrupted cells to remove the cell residues, and removing low-molecular substances through gel filtration.

The culture of the microorganism containing the gene encoding the inosine-guanosine kinase and having the ability to biologically synthesize ATP from the ATP precursor, the cells separated from this culture, or the treated product of the cells is contacted with inosine or guanosine or the precursor thereof in the presence of the energy donor and the phosphate group donor, thereby forming 5'-inosinic acid or 5'-guanylic acid in the reaction solution. The cells can be separated from the culture through centrifugation or the like. The treated product of the cells includes acetone-treated cells, immobilized cells, disrupted cells, etc.

Materials which are preferably used in the present invention are mentioned below.

Examples of the precursor of inosine or guanosine include saccharides such as glucose, sucrose, molasses, starch hydrolysate, etc.; organic acids such as acetic acid. etc.; and alcohols such as glycerol, ethanol, etc.

Examples of the energy donor include saccharides such as glucose, sucrose, starch hydrolysate, molasses, etc.; organic acids such as acetic acid, citric acid, etc.; and alcohols such as ethanol, etc.

Examples of the phosphate group donor include inorganic phosphoric acids such as orthophosphoric acid, pyrophosphoric acid, polyphosphoric acid, tripolyphosphoric acid, polymethaphosphoric acid, hexamethaphosphoric acid, etc.; salts of these inorganic acids; and organic phosphoric acids such as phenyl phosphate, acetyl phosphate, carbamyl phosphate, etc.

The efficiency of the reaction can be improved by adding an ATP precursor, a surfactant, a metal ion, etc., to the reaction solution.

Examples of the ATP precursor include adenosine diphosphate, adenylic acid, adenosine, adenine, adenine mineral acid salt, a ribonucleic acid hydrolysate, etc.

The surfactant may be a cationic, anionic or amphoteric surfactant so far as it enhances the phosphorylation of inosine or guanosine. Examples of the metal ion include magnesium ion, manganese ion, etc.

In the ordinary phosphorylation reaction using a combination of an inosine-guanosine kinase and an ATP-producing strain, an organic solvent is generally added to the reaction system (Japanese Patent Application Laid-Open No. 230, 094/1988 and WO 91/08286). Meanwhile, in the present invention, the reaction proceeds efficiently even when the organic solvent is omitted in the reaction system.

The reaction is aerobically performed at a temperature of from 25 to 37° C. for 10 to 30 hours while adjusting pH between 6 and 8.

After the completion of the reaction, 5'-inosinic acid or 5'-guanylic acid accumulated in the reaction solution can be collected by ion-exchange resin treatment, crystallization, or the like.

BEST MODE OF CARRYING OUT THE INVENTION

The present invention will be described more specifically by referring to the following Examples. However, the present invention is not limited to these Examples.

Example 1

Construction of a Plasmid for Expressing an Inosine-guanosine Kinase Gene Derived From *E. coli* and introduction of the same into *Corynebacterium ammoniagenes*

(1) Amplification of an Inosine-guanosine Kinase Gene by PCR and Cloning Thereof Oligonucleotides having the 5'- and 3'- flanking sequences of the inosine-guanosine kinase gene derived from *E. coli* and restriction endonuclease PstI and HindIII cleavage sites, respectively, as shown in SEQ ID NO:11 and 12, were synthesized by the phosphoramidite method using a DNA synthesizer (Model 394, manufactured by Applied Biosystem Co.)

0.25 $\mu$g these oligonucleotides as primers, 0.1 $\mu$g of chromosomal DNA of *E. coli* W3110 (ATCC 27325) prepared by the method of Saito and Miura (Biochem. Biophys. Acta., 72, 619, (1963)] as a template and 2.5 units of taq DNA polymerase (made by Takara Shuzo Co.) were added to 0.1 ml of 10 mM N-tris(hydroxymethyl)methyl-2-aminoethane (hereinafter referred to as "Tris")-hydrochloride buffer (pH 8.3) containing 200 $\mu$M dATP, 200 $\mu$M dCTP, 200 $\mu$M dGTP, 200 $\mu$M dTTP, 50 mM potassium chloride, 1.5 mM magnesium chloride and 0.0001% gelatin. PCR was carried out in which a three-temperature cycle, namely at 94° C. for 30 seconds, 55° C. for 30 seconds and at 72° C. for 30 seconds was repeated 25 times. The reaction solution was subjected to agarose gel electrophoresis, and the aimed DNA fragment was recovered using a glass powder (made by Takara Shuzo Co.) Approximately 2 $\mu$g of this DNA fragment, 20 units of endonuclease PstI and 20 units of HindIII were mixed with 50 mM Tris-hydrochloride buffer (pH 7.5) containing 10 mM magnesium chloride, 100 mM sodium chloride and 1 mM dithiothreitol, and the mixture was incubated at 37° C. for 2 hours. This digest was extracted with phenol and precipitated with ethanol in a usual manner.

One microgram of plasmid pHSG298 (made by Takara Shuzo Co.) DNA, 20 units of restriction endonuclease PstI and 20 units of restriction endonuclease HindIII were mixed with 50 mM Tris-hydrochloride buffer (pH 7.5) containing 10 mM magnesium chloride, 100 mM sodium chloride and 1 mM dithiothreitol, and the mixture was incubated at 37° C. for 2 hours. After the completion of the incubation, the reaction mixture was extracted with phenol and precipitated with ethanol in a usual manner to obtain plasmid pHSG298 digested with PstI and HindIII. 0.1 μg of this pHSG298 digested with PstI and HindIII, 0.5 μg of the PCR-amplified fragment digested with PstI and HindIII and 1 unit of T4 DNA ligase were added to 66 mM Tris-hydrochloride buffer (pH 7.5) containing 6.6 mM magnesium chloride, 10 mM dithiothreitol and 10 mM ATP, and the mixture was incubated at 16° C. for 8 hours to ligate the DNA. Subsequently, E. coli JM109 (made by Takara Shuzo Co.) was transformed with this DNA mixture in a usual manner, and was inoculated on an L-agar plate medium containing 100 μg/ml of kanamycin to give transformants.

Plasmids were extracted from the thus-obtained transformants by the alkaline lysis method described in Molecular Cloning 2nd edition, by J. Sambrook, E. F. Fritsch and T. Maniatis, Cold Spring Harbour Laboratory Press, p. 1.25 (1989), and were subjected to agarose gel electrophoresis in a usual manner. The recombinant plasmid in which the inosine-guanosine kinase gene was inserted into plasmid pHSG298 was selected. This plasmid was designated "pIGK-1".

(2) Insertion of trp Promoter of E. coli

An oligonucleotide having restriction endonuclease BamHI and PstI cleavage sites at the 5'- and 3'-terminals, respectively, as shown in SEQ ID NO:15, and an oligonucleotide having the complementary sequence were synthesized. These oligonucleotides in amounts of 1 μg each were mixed, treated at 100° C. for 5 minutes, and then cooled gradually to be annealed. This oligonucleotide solution and 20 units of BamHI were mixed with 20 mM Tris-hydrochloride buffer (pH 8.5) containing 10 mM magnesium chloride, 100 mM potassium chloride and 1 mM dithiothreitol, and the mixture was incubated at 30° C. for 2 hours. The resulting digest was extracted with phenol, and precipitated with ethanol. After thus-obtained precipitate was digested with PstI in the same manner as in (1), the digest was extracted with phenol, and the extract was precipitated with ethanol to obtain the DNA fragment containing trp promoter of E. coli and cleaved with BamHI and PstI.

One microgram of recombinant plasmid pIGK-1 containing the inosine-guanosine kinase gene obtained in (1) was likewise digested with BamHI and PstI. The reaction solution was extracted with phenol and precipitated with ethanol in a usual manner to obtain- the plasmid digested with BamHI and PstI. 0.1 pg of this pIGK-1 digested with BamHI and PstI, 0.5 pg of the above-obtained fragment digested with BamHI and PstI and 1 unit of T4 DNA ligase (made by Takara Shuzo Co.) were added to 66 mM Tris-hydrochlcride buffer (pH 7.5) containing 6.6 mM magnesium chloride, 10 mM dithiothreitol and 10 mM ATP, and the mixture was incubated at 16° C. for 8 hours to ligate the DNA. Subsequently, E. coli JM109 (made by Takara Shuzo Co.) was transformed with this DNA mixture, and was inoculated on an L-agar plate medium containing 100 pg/ml of kanamycin to obtain transformants.

Plasmids were extracted from the thus-obtained transformants by the alkaline lysis method, and was subjected to agarose gel electrophoresis in a usual manner to select a recombinant plasmid in which the E. coli trp promoter was inserted in plasmid pIGK-1. This plasmid was designated "pIGK-2".

(3) Insertion of a Replication Origin Derived From Corynebacterium

One microgram of recombinant plasmid pIGK-2 containing the inosine-guanosine kinase gene and the trp promoter obtained in (2) was digested with BamHI in the same manner as in (2), and the digest was extracted with phenol, and the extract was precipitated with ethanol. In order to prevent the re-binding, plasmid pIGK-2 digested with BamHI was subjected to dephosphorylation of the DNA fragment by the treatment using the bacterial alkaline phosphatase according to the method described in Molecular Cloning 2nd edition, by J. Sambrook, E. F. Fritsch and T. Maniatis, Cold Spring Harbour Laboratory Press, p. 1.60 (1989).

Meanwhile, 1 μg of plasmid pHC4 (Japanese Patent Application Laid-Open 7,491/1993) obtained by inserting a region of a replication origin derived from Corynebacterium glutamicum into pHSG399 (made by Takara Shuzo Co.) and 10 units of restriction endonuclease KpnI were added to 10 mM Tris-hydrochloride buffer (pH 7.5) containing 10 mM magnesium chloride and 1 mM dithiothreitol, and the mixture was incubated at 37° C. for 2 hours. The reaction solution was extracted with phenol, and the extract was precipitated with ethanol. The ends of pHC4 cleaved with KpnI were blunted by a prescribed method using a DNA Blunting Kit (made by Takara Shuzo Co.). A phosphorylated BamHI linker (made by Takara Shuzo Co.) was linked with this plasmid using T4 polynucleotide ligase to obtain a DNA fragment having the BamHI cleavage site on both sides of a region containing the plasmid replication origin derived from Corynebacterium glutamicum. This DNA fragment and 20 units of BamHI were mixed in the same buffer as that used in (2), and the mixture was incubated at 30° C. for 2 hours. The reaction solution was extracted with phenol, and the extract was precipitated with ethanol. 0.1 μg of the above-obtained plasmid pIGK-2 digested with BamHI, 0.2 μg of the DNA fragment derived from plasmid pHC4 digested with BamHI and 1 unit of T4 DNA ligase (made by Takara Shuzo Co.) were mixed in the same buffer as that used in (1). The mixture was incubated at 16° C. for 8 hours to ligate the DNA. Subsequently, E. coli JM109 (made by Takara Shuzo Co.) was transformed with this DNA mixture, and was inoculated on an L-agar plate medium containing 100 μg/ml of kanamycin to obtain transformants.

Plasmids were extracted from the thus-obtained transformants by the alkaline lysis, and was subjected to agarose gel electrophoresis in a usual manner to select a recombinant plasmid in which the DNA fragment that is autonomously replicable within Corynebacterium was inserted in plasmid pIGK-2. This plasmid was designated "pIGK-3".

E. coli AJ 12617 containing plasmid pHC4 was deposited at the National Institute of Bioscience and Human Technology of the Agency of Industrial Science and Technology, 1–3, Higashi 1-chome, Tsukuba-shi, Ibaraki-ken 305, Japan, on Apr. 24, 1991 under deposit No. FERM P-12215. It was transferred to deposit under the Budapest Treaty as of Aug. 26, 1991, and was assigned deposit No. FERM BP-3532.

(4) Introduction of pIGK-3 Into Corynebacterium ammoniagenes ATCC 21477

0.1 μg of pIGK-3 obtained in (3) was introduced into Corynebacterium ammoniagenes ATCC 21477 by a usual transformation method using electroporation (Japanese Patent Application Laid-Open No. 207,791/1990). The cells was inoculated on an agar plate medium containing 1% peptone, 1% yeast extract, 0.5% sodium chloride, 0.5% glucose and 50 μg/ml of kanamycin to obtain transformant ATCC 21477/pIGK-3.

(5) Measurement of the Inosine-guanosine Kinase Activity of the Transformant

*Corynebacterium ammoniagenes* ATCC 21477/pIGK-3 obtained in (4) was inoculated in 50 ml of a medium (pH 7.2) containing 1% polypeptone, 1% yeast extract, 5% glucose, 0.4% potassium dihydrogen phosphate, 0.1% magnesium sulfate, 0.5% ammonium sulfate, 0.5% urea, 0.001% ferrous sulfate, 0.001% manganese sulfate, 0.005 g/liter of thiamine hydrochloride, 0.01 *g/liter of calcium pantothenate, 30 μg of biotin, 0.05% adenine and 50 mg/liter of kanamycin, and was cultured at 32° C. for 24 hours. The culture was centrifuged in a usual manner to collect the cells.

A step of suspending the cells in a 0.9% sodium chloride solution and centrifuging the suspension was repeated twice to wash the cells. The resulting cells were suspended in 50 mM Tris-hydrochloride buffer (pH 7.9) containing 20% glycerol, 100 mM potassium chloride and 5 mM 2-mercaptoethanol, and the suspension was sonicated at 150 W for 20 minutes using a device manufactured by Kubota K.K. The thus-treated suspension was centrifuged at 15,000 rpm for 30 minutes to obtain a supernatant. This supernatant was applied to column chromatography using a Sephadex G-15 column (manufactured by Pharmacia Co.) to remove low-molecular weight substances and the resultant solution was used as a crude enzyme solution.

The inosine-guanosine kinase activity of the resulting crude enzyme solution was measured in a reaction mixture containing 100 mM Tris, 10 mM magnesium chloride, 1 mM ATP, 250 mM potassium chloride and 0.2 mM [8-$^{14}$C]-inosine. The crude enzyme solution was added to the reaction mixture, and incubated at 30° C. for 30 minutes. A part of the reaction mixture was spotted on a silica gel plate (manufactured by Merck Co.) to terminate the reaction, and was developed with an eluent containing n-butanol, ethanol and water at a volume ratio of 2:1:1. The spot of 5'-inosinic acid was detected and determined using a Bio-Image Analyzer (manufactured by Fuji Photo Film Co.). The protein concentration of the crude enzyme solution was determined by means of a protein assay kit (manufactured by Bio-Rad Co.) using bovine serum albumin as a standard, and the specific activity of the enzyme was calculated. As a control, the specific activity of ATCC 21477/pHK4, the transformant with plasmid pHK4, was measured. The results are shown in Table 1. *Corynebacterium ammoniagenes* ATCC 21477/pIGK-3 exhibited a high level of the activity, whereas the activity of ATCC 21477/pHK4 was not detected. From these results, it was demonstrated that the introduced gene derived from *E. coli* expressed the inosine-guanosine kinase activity in *Corynebacterium ammoniagenes*.

Plasmid pHK4 has the structure in which the trp promoter and the inosine-guanosine kinase gene are removed from pIGK-3, and was used as a control.

The strain harboring pHK4 in *E. coli* HB101 was designated as AJ 13136 and deposited at National Institute of Bioscience and Human-Technology, Agency of Industrial Science and Technology, 1–3, Higashi 1-chome, Tsukuba-shi, Ibaraki-ken 305, Japan, on August 1, 1995 under the Budapest Treaty with the accession No. FERM BP-5186.

TABLE 1

| Strain | Specific activity (nmol/min/mg · protein) |
| --- | --- |
| ATCC 21477/pHK4 | not detected |
| ATCC 21477/pIGK-3 | 186.6 |

Example 2

Production of 5'-inosinic Acid From Inosine Using the Strain Containing Inosine-guanosine Kinase Gene Derived From *E. coli*

*Corynebacterium ammoniagenes* ATCC 21477/pIGK-3 was inoculated in 450 ml of a medium (pH 7.2) containing 1% polypeptone, 1% yeast extract, 5% glucose, 0.4% potassium dihydrogen phosphate, 0.1% magnesium sulfate, 0.5% ammonium sulfate, 0.5% urea, 0.001% ferrous sulfate, 0.001% manganese sulfate, 0.005 g/liter of thiamine hydrochloride, 0.01 g/liter of calcium pantothenate, 30 μg/liter of biotin, 0.05% adenine and 50 mg/liter of kanamycin, and was cultured at 32° C. for 24 hours. This culture was centrifuged at 7,000 rpm for 10 minutes to obtain 20 g of wet cells as a precipitate.

The thus-obtained cells were suspended in amounts of 200 g/liter in 20 ml of a reaction solution (pH 7.2) containing 50 g/liter of inosine, 20 g/liter of potassium dihydrogen phosphate, 30 g/liter of glucose, 5 g/liter of magnesium sulfate, 10 g/liter of phytic acid (weight ratio 50%), 4 g/liter of Nymeen S-215 and 1 g/liter of adenine. The mixture was incubated at 32° C. with stirring. The pH was adjusted to 7.2 using 4 N sodium hydroxide at times, and a decreased amount of potassium dihydrogen phosphate was added to the reaction mixture. The reaction was conducted using ATCC 21477/pHK4 as a control. After 30 hours of the reaction, the amount of 5'-inosinic acid in the reaction solution was determined by high-performance liquid chromatography. The results are shown in Table 2. The amount of 5'-inosinic acid accumulated was indicated in terms of the amount of disodium 5'-inosinate 7.5-hydrate. From the results, it was found that inosine was converted to 5'-inosinic acid by ATCC 21477/pIGK-3 containing the inosine-guanosine kinase gene derived from *E. coli*.

TABLE 2

| Strain | Amount of 5'-inosinic acid accumulated (g/liter) |
| --- | --- |
| ATCC 21477/pHK4 | not detected |
| ATCC 21477/pIGK-3 | 72.9 |

Example 3

Production of 5'-inosinic Acid From Inosine Using the Strain Containing the Inosine-guanosine Kinase Gene Derived From *E. coli*

The cells obtained in Example 2 was suspended in an amount of 200 g/liter in 50 ml of a reaction solution (pH 7.2) containing 60 g/liter of inosine, 20 g/liter of potassium dihydrogen phosphate, 30 g/liter of glucose, 5 g/liter of magnesium sulfate, 10 g/liter of phytic acid (weight ratio 50%), 4 g/liter of Nymeen S-215 and 1 g/liter of adenine. The mixture was incubated at 32° C. by aerobically stirring.

The pH was adjusted to 7.2 using 4 N sodium hydroxide throughout the reaction by monitoring using a pH meter, and a decreased amount of potassium dihydrogen phosphate was added to the reaction mixture. After 22 hours of the reaction, the accumulation amount of 5'-inosinic acid was 113.8 g/liter, and the molar yield thereof based on inosine added was approximately 100%.

Example 4

Production of 5'-guanylic Acid From Guanosine Using the Strain Containing the Inosine-guanosine Kinase Gene Derived From *E. coli*

The reaction was conducted in the same manner as in Example 2 except that 1 g/liter of guanosine was used instead of inosine in the reaction solution. After 30 hours of the reaction, the amount of 5'-guanylic acid in the reaction mixture was determined by high-performance liquid chromatography. As a result, 0.05 g/liter of 5'-guanylic acid were accumulated as calculated in terms of disodium 5'-guanylate 6.5-hydrate in the reaction mixture using ATCC 2147.7/pIGK-3.

Example 5

Purification of the Protein Having the Inosine-guanosine Kinase Activity From *Exiguobacterium acetylicum* and Properties Thereof (1) Preparation of Cells and a Crude Enzyme Extract

*Exiguobacterium acetylicum* ATCC 953 was inoculated in 100 ml of a medium (pH 7.2) containing 1% polypeptone, 1% bacto yeast extract, 0.5% glucose and 0.5% sodium chloride, and was cultured at 30° C. for 24 hours. This culture was inoculated in 2 liters of the above-mentioned medium, and was incubated at 30° C. for 8 hours. The thus-obtained culture was centrifuged at 7,000 rpm for 10 minutes, and the precipitate was washed twice with 0.9 % sodium chloride to obtain 10 g of wet cells. The cells were suspended in 10 ml of 100 mM Tris-hydrochloride buffer (pH 7.5) containing 100 mM calcium chloride and 1 mM dithiothreitol (buffer A), and was milled by means of a bead beater (manufactured by Biospeck Co.) using glass beads having a diameter of 0.1 mm. The suspension was centrifuged at 15,000 rpm for 1;0 minutes, and the supernatant was dialyzed against the above-mentioned buffer to obtain approximately 20 ml of a crude enzyme extract.

The inosine-guanosine kinase activity of the crude enzyme extract was measured by the following method. Five microliters of the crude enzyme extract were added to 50 p1 of 100 mM Tris-hydrochloride buffer (pH 7.5) containing 5 mM magnesium chloride, 5 mM ATP, 100 mM potassium chloride and 0.2 mM [8-$^{14}$C]-inosine. This reaction mixture was incubated at 30° C. for 30 minutes. Two microliters of the reaction mixture were spotted on a silica-gel plate (manufactured by Merck Co.) to terminate the reaction, and was developed with an eluent containing n-butanol, ethanol and water at a volume ratio of 2:1:1. The spot of 5'-inosinic acid was detected and the amount of 5'-inosinic acid was determined using a Bio-Image Analyzer (manufactured by Fuji Photo Film Co.). The concentration of the protein of the crude enzyme solution was determined by means of a protein assay (manufactured by Bio-Rad Co.) using bovine serum albumin as a standard, and the specific activity of the enzyme was calculated. The inosine-guanosine kinase activity of the crude enzyme extract was 0.45 nmol/min/mg·protein.

(2) Purification of the Protein Having the Inosine-guanosine Kinase Activity

The crude extract obtained in (1) was applied to a DEAE-Toyopearl (made by Tosoh Co.) column which had been equilibrated with the buffer A. After being washed with the buffer A, the protein having the inosine-guanosine kinase activity was eluted with the buffer A containing 200 mM potassium chloride. To 25 ml of the thus-obtained active fraction, ammonium sulfate was added to 30% saturation. After the mixture was stirred at 4° C. for 30 minutes, the precipitate was removed by centrifugation. The resulting supernatant was applied to a Butyl-Toyopearl (made by Tosoh Co.) column which had been equilibrated with the buffer A containing 30% ammonium sulfate. After being washed with the above-mentioned buffer, the protein having the inosine-guanosine kinase activity was eluted using a linear concentration gradient of 200 ml of the buffer A containing from 30% to 15% of ammonium sulfate. Approximately 15 ml of the resulting active fraction were dialyzed against 2 liters of 25 mM Tris-hydrochloride buffer (pH 7.5) containing 50 mM potassium chloride, 1 mM dithiothreitol and 20% glycerol (buffer B).

This solution was centrifuged at 15,000 rpm for 10 minutes, and the resulting supernatant was applied to a MonoQ FPLC HR5/5 (made by Pharmacia Co.) column which had been equilibrated with the buffer B containing 100 mM potassium chloride. After being washed with the buffer B, the protein having the inosine-guanosine kinase activity was eluted using a linear concentration gradient of ammonium sulfate from 100 mM to 500 mM. The thus-obtained active fraction was dialyzed against 2 liters of 10 mM potassium phosphate buffer (pH 7.4) containing 1 mM dithiothreitol and 20% glycerol (buffer C), and was applied to a hydroxylapatite TSK-GEL HA-1000 (made by Tosoh Co.) column which had been equilibrated with the above-mentioned buffer. After being washed with the above-mentioned buffer, the protein having the inosine-guanosine kinase activity was eluted using a linear concentration gradient of 30 ml of the buffer C containing from 10 mM to 500 mM of potassium phosphate.

Approximately 6 ml of the thus-obtained active fraction was repeatedly applied to the hydroxylapatite column, and the protein having the inosine-guanosine kinase activity was eluted using a linear concentration gradient of 30 ml of the buffer C containing from 10 mM to 200 mM of potassium phosphate. Two milliliters of the fraction with high activity among the thus-obtained active fractions were applied to a gel filtration Hiload Superdex 200pg 16/60 (made by Pharmacia Co.) column which had been equilibrated with 25 mM Tris-hydrochloride buffer (pH 7.5) containing 1 mM dithiothreitol, 20% glycerol and 100 mM potassium chloride, and were eluted with the above-mentioned buffer. Five microliters of 2 ml of the fraction with high activity were subjected to SDS polyacrylamide gel electrophoresis. As a result, a protein having a molecular weight of approximately 36 kilodaltons was detected by the silver staining (Nacalai Tesque Co.). Thus, the protein having the activity of the inosine-guanosine kinase derived from *Exiguobacterium acetylicum* was purified, and the molecular weight thereof was found to be 36 kilodaltons as measured by SDS-polyacrylamide gel electrophoresis.

(3) Properties of the Inosine-guanosine Kinase Derived From *Exiguobacterium acetylicum*

The purified inosine-guanosine kinase was added to 100 mM Tris-hydrochloride buffer (pH 7.5) containing 5 mM magnesium chloride, 5 mM ATP, 100 mM potassium chloride, 0.16 mM guanosine and 0.04 mM [8-$^{14}$ C]-guanosine. Fifty microliter of this reaction mixture was used as a basic composition and the reaction was carried out at 30° C. for 10 minutes. The enzyme had the following properties.

1. Action

The enzyme transfers a phosphate group to a nucleoside selected from the group consisting of guanosine, inosine and 2'-deoxyguanosine using as a phosphate donor a nucleoside triphosphate selected from the group consisting of ATP, 2'-deoxyadenosine triphosphate, guanosine triphosphate, 2'-deoxyguanosine triphosphate and thymidine triphosphate, and it forms a 5'-monophosphate of the nucleoside selected from the group consisting of 5'-guanylate, 5'-inosinate and 2'-deoxy-5'-guanylate, respectively.

2. Substrate Specificity

The reaction was performed by using 0.5 mM of each of various nucleosides instead of guanosine and [Y-$^{32}$P]-ATP instead of ATP. The thus-formed nucleoside 5'-phosphate was measured. The results are shown in Table 3. Guanosine, inosine and 2'-deoxyguanosine were used as a phosphate receptor.

TABLE 3

| Nucleoside (0.5 mM) | Relative activity (%) |
| --- | --- |
| guanosine | 100 |
| 2'-deoxyguanosine | 4 |
| inosine | 5 |
| xanthosine | 0 |
| adenosine | 0 |
| 2'-deoxyadenosine | 0 |

The reaction was performed by using 5 mM of each of various nucleoside triphosphates instead of ATP, and the possible phosphate donors were examined. The results are shown in Table 4.

Besides ATP, 2'-deoxyadenosine triphosphate, guanosine triphosphate, 2'-deoxyguanosine triphosphate and thymidine triphosphate were used as the phosphate donor.

TABLE 4

| Nucleoside triphosphate (5 mM) | Relative activity (%) |
| --- | --- |
| adenosine triphosphate | 100 |
| 2'-deoxyadenosine triphosphate | 71 |
| guanosine triphosphate | 59 |
| 2'-deoxyguanosine triphosphate | 61 |
| cytidine triphosphate | 6 |
| uridine triphosphate | 4 |
| thymidine triphosphate | 35 |
| not added | 0 |

3. Optimum pH

The reaction was performed by changing the buffer to 100 mM of sodium acetate-acetic acid buffer (pH 4.2–5.6), 2-morphorinoethanesulfonic acid (hereinafter referred to as "MES")-sodium hydroxide buffer (pH 5.4–6.3), 3-morphorinopropanesulfonic acid (MOPS)-sodium hydroxide buffer (pH 6.3–7.2), Tris-hydrochloride buffer (pH 7.2–8.8), cyclohexylaminopropanesulfonic acid (hereinafter referred to as "CAPS")- sodium hydroxide buffer (pH 8.8–10.4) or glycine-sodium hydroxide buffer (pH 10.3–11.0). The optimum pH was between 7.7 and 9.9.

4. pH Stability

The enzyme was treated at room temperature for 30 minutes with 250 mM sodium acetate-acetate buffer (pH 1.5–5.6), MES-sodium hydroxide buffer (pH 5.4–6.4), MOPS-sodium hydroxide buffer (pH 6.3–7.3), Tris-hydrochloride buffer (pH 7.2–8.8), CAPS-sodium hydroxide buffer (pH 8.9–10.4) or glycine-sodium hydroxide buffer (pH 10.5–13.3), each containing 2.5 mg/ml of bovine- serum albumin, 25 mM potassium chloride, 0.25 mM dithiothreitol and 5% glycerol. Then, the activity of the enzyme was measured. As a result, the activity of the enzyme was stable within the pH range between 6.7 and 12.1

5. Optimum Temperature

The reaction was performed within the temperature range between 16° C. and 60° C. As a result, the optimum temperature was between 30° C. to 50° C.

6. Temperature Stability

The enzyme was treated with 12.5 mM Tris-hydrochloride buffer (pH 7.5) containing 5 mg/ml of bovine serum albumin, 50 mM potassium chloride, 0.5 mM dithiothreitol and 10% glycerol at 4 to 60° C. for 30 minutes, and the residual activity of the enzyme was measured. The activity of 50% or more was maintained upon the treatment at 25° C. or lower, and the enzyme was inactivated at 40° C. or higher.

7. Metal Requirement

The reaction was performed by changing magnesium chloride to various metal ions in the reaction solution. The results are shown in Table 5. It was found that the metal ions were required for the activity, and that the reaction proceeded with manganese ions, cobalt ions and iron ions other than magnesium ions.

TABLE 5

| Metal salts (5 mM) | Relative activity (%) |
| --- | --- |
| not added | 1 |
| MgCl$_2$.6H$_2$O | 100 |
| MnCl$_2$.4H$_2$O | 55 |
| ZnCl$_2$ | 1 |
| NiCl$_2$.6H$_2$O | 1 |
| CaCl$_2$.2H$_2$O | 1 |
| CoCl$_2$.6H$_2$O | 36 |
| MgSo$_2$.7H$_2$O | 107 |
| FeSO$_2$.7H$_2$O | 24 |

8. Effect of Metal Ions

The relative activity of the enzyme in the presence of 1 mM of various metal ions in the reaction mixture is shown in Table 6. The enzyme was strongly inhibited by copper ions and mercury ions, and was also inhibited by zinc ions and cadmium ions.

TABLE 6

| Metal salts (1 mM) | Relative viscosity (%) |
| --- | --- |
| not added | 100 |
| MnCl$_2$.4H$_2$O | 81 |
| ZnCl$_2$ | 58 |
| NiCl$_2$.6H$_2$O | 113 |
| CaCl$_2$.2H$_2$O | 71 |
| CoCl$_2$.6H$_2$O | 103 |
| BaCl$_2$ | 106 |
| CuCl$_2$.2H$_2$O | 25 |
| CdCl$_2$ | 43 |
| HgCl$_2$ | 22 |
| MgSO$_4$.7H$_2$O | 110 |
| FeSO$_4$.7H$_2$O | 95 |

9. Km Values

The Km values of the enzyme which were measured by changing the substrate concentration of the reaction composition were 0.03 mM for guanosine, 1 mM for inosine, and 1.6 mM for ATP when guanosine was used as a substrate.

10. Molecular Weight

The enzyme had a molecular weight of approximately 36 kilodaltons as measured by SDS-polyacrylamide gel electrophoresis.

Example 6

Isolation of the Gene From the Chromosome of *Exiguobacterium acetylicum*

(1) Determination of an N-terminal Amino-acid Sequence

Approximately 2 ml of the active fraction obtained in Example 5 (2) was concentrated to approximately 0.2 ml through centrifugation at 6,000 rpm for 3 hours using Centricon-10 (manufactured by Amicon Co.). The protein was blotted on a filter through centrifugation using Prospin (manufactured by Applied Biosystem Co.). This filter was washed three times with 20% methanol, and then dried. The N-terminal amino-acid sequence of the protein was determined using a protein sequencer 476A (manufactured by Applied Biosystem Co.). The amino-acid sequence determined is represented by SEQ ID NO:3 in Sequence Listing. In this Sequence Listing, Xaa represents an unidentified amino acid. Twenty-eight amino acids including one unidentified amino acid at the N-terminal were determined.

(2) Preparation of Chromosomal DNA of *Exiguobacterium acetylicum* and Amplification of the N-terminal Region Three grams of wet cells of *Exiguobacterium acetylicum* ATCC 953 were obtained from 500 ml of the culture in the same manner as in Example 5 (1). Chromosomal DNA was extracted from the cells by the method of Saito and Miura [Biochem. Biophys. Acta., 72, 619, (1963)]

According to the N-terminal amino-acid sequence obtained in (1), oligonucleotides -were synthesized. With respect to the nucleotide sequences, mixtures of oligonucleotides shown in SEQ ID NO: 4 and 5 were used in consideration of degeneracy of codons.

0.25 μmols of the oligonucleotides as primers, 0.1 μg of chromosomal DNA of *Exiguobacterium acetylicum* as a template and 2.5 units of taq DNA polymerase (made by Takara Shuzo Co.) were added to 0.1 ml of 10 mM Tris-hydrochloride buffer (pH 8.3) containing 200 μM dATP, 200 μM dCTP, 200 μM dGTP, 200 μM dTTP, 50 mM potassium chloride, 1.5 mM magnesium chloride and 0.0001 % gelatin. PCR was performed in which a three-temperature cycle, namely at 94° C. for 30 seconds, at 55° C. for 30 seconds and at 72° C. for 1 minute was repeated 30 times. The reaction solution was subjected to agarose gel electrophoresis, and the amplified DNA fragment having a length of approximately 80 bases was recovered using a glass powder (made by Takara Shuzo Co.). Approximately 0.2 μg of this DNA fragment were added to 50 μl of 50 mM Tris-hydrochloride buffer (pH 7.5) containing 2 units of Klenow fragment, 200 μM dATP, 200 μM dCTP, 200 μM dGTP, 200 μM dTTP, 1 mM 2-mercaptoethanol and 7 mM magnesium chloride. The mixture was subjected to a blunting reaction at 37° C. for 30 minutes. The reaction mixture was extracted with phenol, and the extract was precipitated with ethanol. The thus-precipitated DNA fragment having the blunt ends was dissolved in 50 mM Tris-hydrochloride buffer (pH 7.6) containing 10 units of T4 polynucleotide kinase, 10 mM magnesium chloride, 5 mM dithiothreitol, 0.1 mM spermidine and 0.1 mM EDTA, and was subjected to a reaction of phosphorylating ends at 37° C. for 1 hour. The reaction mixture was extracted with phenol, and the extract was precipitated with ethanol. The PCR product having the phosphorylated blunt ends was recovered as a precipitate.

One micrograms of plasmid vector pUC18 (made by Takara Shuzo Co.) and 20 units of restriction endonuclease SmaI were mixed with 33 mM Tris-acetate buffer (pH 7.9) containing 10 mM magnesium acetate, 66 mM potassium acetate, 0.5 mM dithiothreitol and 0.01% bovine serum albumin, and the mixture was incubated at 30° C. for 2 hours to obtain a digest. This digest was extracted with phenol and precipitated with ethanol in a usual manner. Then, in order to prevent the re-binding of the DNA fragment derived from the plasmid vector, the DNA fragment was dephosphorylated. The resulting fragment was extracted with phenol and precipitated with ethanol in a usual manner. 0.1 μg of this pUC18 digested with SmaI, 0.1 μg of the PCR product having the phosphorylated blunt ends and 1 unit of T4 DNA ligase (made by Takara Shuzo Co.) were added to 20 μl of 66 mM Tris-hydrochloride buffer (pH 7.5) containing 6.6 mM magnesium chloride, 10 mM dithiothreitol and 10 mM ATP. The mixture was incubated at 16° C. for 8 hours to ligate the DNA. Subsequently, *E. coli* JM109 (made by Takara Shuzo Co.) was transformed with the DNA mixture in a usual manner, and was inoculated on an L-agar medium containing 100 μg/ml of ampicillin to obtain transformants.

Plasmids were extracted from the transformants by the alkaline lysis method.

The plasmids contained a DNA fragment of approximately 80 bases derived from the chromosomal DNA of Exiguobacterium acetylicum ATCC 953. The nucleotide sequence of the DNA fragment was determined using this plasmid DNA. The determination of the nucleotide sequence was conducted according to the method of Sanger [J. Mol. Biol., 143, 161 (1980)] using Taq DyeDeoxy Terminator Cycle Sequencing Kit (made by Perkin Elmer Co.) Thus, the nucleotide sequence of 83 bases of the DNA corresponding to the N-terminal region of the inosine-guanosine kinase protein of *Exiguobacterium acetylicum* ATCC 953 was determined.

(3) Isolation of the DNA Fragment Containing the Gene Encoding the Inosine-guanosine Kinase of *Exiguobacterium acetylicum*

Ten micrograms of the chromosomal DNA of *Exiguobacterium acetylicum* ATCC 953 prepared in (2) were added to 50 mM Tris-hydrochloride buffer (pH 7.5) containing 40 units of SRI, 10 mM magnesium chloride, 100 mM sodium chloride and 1 mM dithiothreitol, and the mixture was incubated at 37° C. for 2 hours. The reaction mixture was extracted with phenol and precipitated with ethanol in a usual manner to obtain the chromosomal DNA of *Exiguobacterium acetylicum* ATCC 953 digested with EcoRI. One microgram of this DNA digested with EcoRI, 0.05 μg of EcoRI cassette (made by Takara Shuzo Co.) and 10 units of T4 DNA ligase were added to 66 mM Tris-hydrochloride buffer (pH 7.5) containing 6.6 mM magnesium chloride, 10 mM dithiothreitol and 10 mM ATP. The mixture was incubated at 16° C. for 8 hours to ligate the DNA. The reaction mixture was extracted with phenol, and the extract was precipitated with ethanol to obtain the chromosomal DNA digest of *Exiguobacterium acetylicum* ATCC 953 ligated with EcoRI cassette.

Oligonucleotides S1 and S2 having the nucleotide sequences shown in SEQ ID NO:6 and 7 were synthesized according to the sequence determined in (2).

0.2 μmols of oligonucleotide S1 and 0.2 μmols of cassette primer C1 (made by Takara Shuzo Co.) as primers, 0.2 μg of the chromosomal DNA digest of *Exiguobacterium acetylicum* ATCC 953 ligated with EcoRI cassette as a template and 2.5 units of taq DNA polymerase (made by Takara Shuzo Co.) were added to 0.1 ml of 10 mM Tris-hydrochloride-buffer (pH 8.3) containing 200 μM dATP, 200 μM dCTP, 200 μM dGTP, 200 μM dTTP, 50 mM potassium chloride, 1.5 mM magnesium chloride and 0.0001% gelatin.

PCR was performed in which a three-temperature cycle, namely at 94° C. for 30 seconds, at 55° C. for 2 minutes and at 72° C. for 3 minutes was repeated 25 times. PCR was performed under the above-mentioned conditions using 1 μl of the reaction mixture as a template, and 0.2 μmols of oligonucleotide S2 and 0.2 μmols of cassette primer C2 (made by Takara Shuzo Co.) as primers. A part of the reaction mixture was subjected to agarose gel electrophoresis. As a result, a fragment of approximately 1,000 base pairs was specifically amplified. The DNA fragment extending from the N-terminal region of the protein to the EcoRI cleavage site in downstream of the gene was obtained.

This DNA fragment was recovered using a glass powder (made by Takara Shuzo Co.). Approximately 0.2 μg of this DNA fragment were subjected to a blunting reaction at 37° C. for 30 minutes using Klenow fragment. The reaction mixture was extracted with phenol, and the extract was precipitated with ethanol. The DNA fragment recovered as a precipitate was subjected to a reaction of phosphorylating ends at 37° C. for 1 hour using T4 polynucleotide kinase. The reaction mixture was extracted with phenol, and the extract was precipitated with ethanol. The PCR product having the phosphorylated blunt ends were recovered as a precipitate.

One microgram of plasmid vector pUC18 (made by Takara Shuzo Co.) was treated with restriction endonuclease SmaI at 30° C. for 2 hours to obtain a digest. This digest was extracted with phenol and precipitated with ethanol in a usual manner. Subsequently, the DNA fragment was dephosphorylated by the treatment with bacterial alkaline phosphatase, extracted with phenol, and precipitated with ethanol.

0.1 μg of this pUC18 digested with SmaI, 0.1 μg of the PCR product having the phosphorylated blunt ends and 1 unit of T4 DNA ligase (made by Takara Shuzo Co.) were reacted at 16° C. for 8 hours to ligate the DNA. Then, *E. coli* JM109 (made by Takara Shuzo Co.) was transformed with this DNA mixture, and inoculated on an L-agar plate medium-containing 100 μg/ml of ampicillin to obtain transformants.

Plasmids were extracted from the thus-obtained transformants by the alkaline lysis method and the plasmid containing the PCR-amplified fragment was selected. This plasmid was designated "pCS2".

Oligonucleotides complementary to the oligonucleotides Si and S2 were synthesized and designated S4 and S3 respectively. The amplification was performed by PCR under the same conditions as mentioned above using oligonucleotide S3 and cassette primer C1 (made by Takara Shuzo Co.) as primers and the chromosomal DNA digest of *Exiguobacterium acetylicum* ATCC 953 ligated with EcoRI cassette as a template. PCR was performed using the thus-obtained reaction mixture as a template and oligonucleotide S4 and cassette primer C2 (made by Takara Shuzo Co.) as primers. The DNA fragment of approximately 2,300 base pairs extending from the N-terminal region of the protein to the EcoRI cleavage site in upstream of the gene was amplified.

Approximately 0.2 μg of this DNA fragment were subjected to a blunting reaction at 37° C. for 30 minutes using Klenow fragment. The reaction mixture was extracted with phenol, and the extract was precipitated with ethanol. The DNA fragment recovered as a precipitate was mixed with 50 μl of 10 mM Tris-hydrochloride buffer (pH 7.5) containing 10 units of restriction endonuclease KpnI, 10 mM magnesium chloride and 1 mM dithiothreitol. The mixture was incubated at 37° C. for 2 hours to obtain a digest. The digest was extracted with phenol, and the extract was precipitated with ethanol.

One microgram of plasmid vector pUC18 (made by Takara Shuzo Co.), 5 units of restriction endonuclease KpnI and 5 units of restriction endonuclease HincII were mixed with 50 μl of 33 mM Tris-acetate buffer (pH 7.9) containing 10 mM magnesium chloride, 50 mM sodium chloride and 1 mM dithiothreitol. The mixture was incubated at 37° C. for 2 hours to obtain a digest. The digest was extracted with phenol, and the extract was precipitated with ethanol.

0.1 μg of this pUC18 digested with KpnI and HincII, approximately 0.1 μg of the PCR product subjected to the blunting reaction and digested with KpnI were reacted using T4 DNA ligase (made by Takara Shuzo Co.) at 16° C. for 8 hours to ligate the DNA. Then, *E. coli* JM109 (made by Takara Shuzo Co.) was transformed with this DNA mixture, and inoculated on an L-agar plate medium containing 100 μg/ml of ampicillin to obtain transformants.

Plasmids were extracted from the thus-obtained transformants through the alkaline lysis method. A plasmid containing a DNA fragment of approximately 600 base pairs extending from the N-terminal region of the protein to the KpnI cleavage site in upstream of the gene was selected. This plasmid was designated "pKS4".

(4) Determination of the Nucleotide Sequence of the Inosine-guanosine Kinase Gene of *Exiguobacterium acetylicum*

The nucleotide sequences of plasmids pCS2 and pKS4 obtained in (3) were determined. The nucleotide sequence of the open reading frame to be presumed therefrom is represented by SEQ ID NO:1 in Sequence Listing. The amino-acid sequence of the product to be presumed from this nucleotide sequence is represented by SEQ ID NO:2 in Sequence Listing. That is, the gene encoding the protein having the amino-acid sequence represented by SEQ ID NO:2 in Sequence Listing is the inosine-guanosine kinase gene of *Exiguobacterium acetylicum* ATCC 953.

The nucleotide sequence and the amino-acid sequence were compared with the known sequences with respect to homology. EMBL and SWISS-PROT were used as data base. As a result, it was found that the DNA represented by SEQ ID NO:1 in Sequence Listing and the protein encoded by this DNA are novel, and that the nucleotide sequence is less homologous to the sequence encoding the *E. coli* inosine-guanosine kinase which is the only one known as a gene encoding the inosine-guanosine kinase, and is quite different therefrom.

The protein encoded by this gene was composed of 303 amino acids, and the molecular weight of the protein presumed from the amino acid sequence was 32.5 kilodaltons.

Example 7

Construction of a Plasmid for Expressing the Inosine-guanosine Kinase Derived From *Exiguobacterium acetylicum* ATCC 953 and Introduction of the Same Into *Corynebacterium ammoniagenes*

(1) Amplification of the Inosine-guanosine Kinase Gene by PCR and Cloning Thereof Oligonucleotides having the 5'- and 3'- flanking sequence of the inosine-guanosine kinase gene of *Exiguobacterium acetylicum* and restriction endonuclease PstI and SphI cleavage sites, respectively, as shown in SEQ ID NO:8 and 9 were synthesized.

0.25 lumoles of these oligonucleotides as primers, 0.1 μg of the chromosomal DNA of *Exiguobacterium acetylicum* ATCC 953 prepared in Example 6 (2) as a template and 2.5 units of taq DNA polymerase (made by Takara Shuzo Co.) were added to 0.1 ml of 10 mM Tris-hydrochloride buffer (pH 8.3) containing 200 μM dATP, 200 μM dCTP, 200 μM dGTP, 200 μM dTTP, 50 mM potassium chloride, 1.5 mM magnesium chloride and 0.0001% gelatin. PCR was carried out in which a three-temperature cycle, namely at 94° C. for 30 seconds, at 55° C. for 30 seconds and at 72° C. for 30 seconds, was repeated 25 times. The reaction mixture was subjected to agarose gel electrophoresis, and the aimed DNA fragment was recovered using a glass powder (made by Takara Shuzo Co.). Approximately 2 μg of this DNA fragment, 10 units of restriction endonuclease PstI and 10 units of restriction endonuclease SphI were mixed with 50 μl of 50 mM Tris-hydrochloride buffer (pH 7.5) containing 10 mM magnesium chloride, 100 mM sodium chloride and 1 mM dithiothreitol. The mixture was incubated at 37° C. for 2 hours to obtain a digest. This digest was extracted with phenol, and the extract was precipitated with ethanol.

One microgram of plasmid pHSG298 (made by Takara Shuzo Co.), 20 units of restriction endonuclease PstI and 20 units of restriction endonuclease SphI were mixed with 50 mM Tris-hydrochloride buffer (pH 7.5) containing 10 mM magnesium chloride, 100 mM sodium chloride and 1 mM dithiothreitol. The mixture was incubated at 37° C. for 2 hours. The reaction mixture was extracted with phenol and precipitated with ethanol in a usual manner to obtain plasmid pHSG298 digested with PstI and SphI. 0.1 μg of this plasmid pHSG298 digested with PstI and SphI, 0.5 μg of the PCR-amplified fragment digested with PstI and SphI and 1 unit of T4 DNA ligase (made by Takara Shuzo Co.) were added to 66 mM Tris-hydrochloride buffer (pH 7.5) containing 6.6 mM magnesium chloride, 10 mM dithiothreitol and 10 mM ATP. The mixture was incubated at 16° C. for 8 hours to ligate the DNA. Subsequently, E. coli JM109 (made by Takara Shuzo Co.) was transformed with this DNA mixture in a usual manner, and was inoculated on an L-agar plate medium containing 100 μg/ml of kanamycin to obtain transformants.

Plasmids were extracted from the thus-obtained transformants by the alkaline lysis method, and was subjected to agarose gel electrophoresis. A recombinant plasmid in which the inosine-guanosine kinase gene derived from *Exiguobacterium acetylicum* was inserted into vector plasmid pHSG298 was selected. This plasmid was designated "pBA-1".

(2) Insertion of *E. coli* Trp Promoter

A DNA fragment containing *E. coli* trp promoter cleaved with BamHI and PstI was prepared in the same manner as in Example 1 (2).

One microgram of the recombinant plasmid pBA-1 having inserted therein the DNA fragment containing the inosine-guanosine kinase gene as obtained in (1) was digested with BamHI and PstI. The reaction mixture was extracted with phenol and precipitated with ethanol in a usual manner to obtain a plasmid digested with BamHI and PstI. 0.1 μg of this plasmid digested with BamHI and PstI were ligated with the DNA fragment containing the *E. coli* trp promoter digested with BamHI and PstI using 1 unit of T4 DNA ligase (made by Takara Shuzo Co.). Subsequently, *E. coli* JM109 (made by Takara Shuzo Co.) was transformed with this ,DNA mixture, and was inoculated on a L-agar plate medium containing 100 μg/ml of kanamycin to obtain transformants.

Plasmids were extracted from the thus-obtained transformants, and were subjected to agarose gel electrophoresis. A recombinant plasmid in which the *E. coli* trp promoter was inserted into the plasmid pBA-1 was selected. This plasmid was designated "pBA-2".

*E. coli* AJ 13094 containing plasmid pBA-2 was deposited at National Institute of Bioscience and Human Technology, Agency of Industrial Science and Technology, 1–3, Higashi 1 chome, Tsukuba-shi, Ibaraki-ken 305, Japan, on Apr. 27, 1995 under the Budapest Treaty with the accession No. FERM BP-5089.

(3) Insertion of a Replication Origin Derived From a Bacterium of the Genus Corynebacterium In the same manner as in (2), 1 μg of recombinant plasmid pBA-2 containing the inosine-guanosine kinase gene and the trp promoter obtained in (2) was digested with BamHI. The digest was extracted with phenol, and the extract was precipitated with ethanol. The precipitate was digested with KpnI in the same manner as in Example 6 (2), and the digest was extracted with phenol, and the extract was precipitated with ethanol. The thus-obtained plasmid pBA-2 digested with BamHI and KpnI was subjected to dephosphorylation of the DNA fragment through the bacterial phosphatase treatment. The resulting substance was extracted with phenol, and the extract was precipitated with ethanol.

Meanwhile, 1 μg of plasmid pHC4 (Japanese Patent Application Laid-Open 7,491/1993) was digested likewise with BamHI and KpnI. The digest was extracted with phenol, and the extract was precipitated with ethanol. 0.1 μg of the above-obtained plasmid pBA-2 digested with BamHI and KpnI was ligated with 0.2 μg of the DNA fragment derived from the plasmid pHC4 digested with BamHI and KpnI using T4 DNA ligase (made by Takara Shuzo Co.) Subsequently, *E. coli* JM109 (made by Takara Shuzo Co.) was transformed with this DNA mixture, and was inoculated on an L-agar plate medium containing 100 μg/ml of kanamycin to obtain transformants.

Plasmids were extracted from the thus-obtained transformants by the alkaline lysis method, and was subjected to agarose gel electrophoresis. A recombinant plasmid in which the replication origin derived from a bacterium of the genus Corynebacterium was inserted into plasmid pBA-2 was selected. This plasmid was designated "pBA-3".

(4) Introduction of pBA-3 into *Corynebacterium ammoniagenes* ATCC 21477

0.1 μg of pBA-3 obtained in (3) was introduced into *Corynebacterium ammoniagenes* ATCC 21477 by the usual electroporation method (Japanese Patent Application Laid-Open No. 207,791/1990). The transformed cells were inoculated on an agar medium containing 1% peptone, 1% yeast extract, 0.5% sodium chloride, 0.5% glucose and 50 μg/ml of kanamycin to obtain the transformant ATCC 21477/pBA-3.

(5) Measurement of the Inosine-guanosine Kinase Activity of the Recombinant Strain

*Corynebacterium ammoniagenes* ATCC 21477/pBA-3 obtained in (4) was inoculated in 50 ml of a medium (pH 7.2) containing 1% polypeptone, 1% yeast extract, 5% glucose, 0.4% potassium dihydrogen phosphate, 0.1% magnesium sulfate, 0.5% ammonium sulfate, 0.5% urea, 0.001% ferrous sulfate, 0.001% manganese sulfate, 0.005 g/liter of thiamine hydrochloride, 0.01 g/liter of calcium pantothenate, 30 μg/liter of biotin, 0.05% adenine and 50 mg/liter of kanamycin, and was cultured at 32° C. for 24 hours. The culture was centrifuged in a usual manner to collect the cells.

A step of suspending the cells in 0.9% sodium chloride aqueous solution and centrifuging the suspension was repeated twice to wash the cells. The resulting cells were suspended in 50 mM Tris-hydrochloride buffer (pH 7.9) containing 20% glycerol and 100 mM potassium chloride, and the suspension was sonicated at 150 W for 20 minutes and then centrifuged at 15,000 rpm for 30 minutes to obtain a supernatant. This supernatant was applied to a Sephadex G-15 column (made by Pharmacia Co.) to remove low-molecular substances and the resultant solution was used as a crude enzyme solution.

The inosine-guanosine kinase activity of the crude enzyme solution was measured by the method described in Example 5 (1). At this time, ATCC 21477/pHK4 which was obtained by the transformation with plasmid pHK4 was used as a control. The results are shown in Table 7. ATCC 21477/pBA-3 exhibited a high level of the activity, whereas no activity was observed in ATCC 21477/pHK4. From these results, it was demonstrated that the introduced gene derived from *Exiguobacterium acetylicum* expressed inosine-guanosine kinase activity in *Corynebacterium ammoniagenes*.

Plasmid pHK4 was used as a control because it has a structure in which the trp promoter and inosine-guanosine kinase gene regions are removed from pBA-3.

The strain harboring pHK4 in *E. coli* HB101 was designated as AJ 13136 and deposited at National Institute of Bioscience and Human-Technology, Agency of Industrial Science and Technology, 1–3, Higashi 1 chome, Tsukuba-shi, Ibaraki-ken 305, Japan, on August 1, 1995 under the Budapest Treaty with the accession No. FERM BP-5186.

TABLE 7

| Strain | Specific activity (nmol/min/mg · protein) |
| --- | --- |
| ATCC 21477/pHK4 | not detected |
| ATCC 21477/pBA-3 | 50.4 |

Example 8

Production of 5'-inosinic Acid From Inosine Using the Cells Containing the Inosine-guanosine Kinase Gene of *Exiguobacterium acetylicum*

*Corynebacterium ammoniagenes* ATCC 21477/pBA-3 was inoculated in 450 ml of a medium (pH 7.2) containing 1% polypeptone, 1% yeast extract, 5% glucose, 0.4% potassium dihydrogen phosphate, 0.1% magnesium sulfate, 0.5% ammonium sulfate, 0.5% urea, 0.001% ferrous sulfate, 0.001% manganese sulfate, 0.005 g/liter of thiamine hydrochloride, 0.01 g/liter of calcium pantothenate, 30 µg/liter of biotin, 0.05% adenine and 50 mg/liter of kanamycin, and was cultured at 32° C. for 24 hours. The resulting culture was centrifuged at 7,000 rpm for 10 minutes, to collect 20 g of wet cells as a precipitate.

The thus-obtained cells were suspended in amounts of 200 g/liter in 20 ml of a reaction solution (pH 7.2) containing 50 g/liter of inosine, 20 g/liter of potassium dihydrogen phosphate, 30 g/liter of glucose, 5 g/lite of magnesium sulfate, 10 g/liter of phytic acid (weight ratio of 50%), 4 g/liter of Nymeen S-215 and 1 g/liter of adenine. The suspension was incubated at 32° C. with stirring. The pH was adjusted to 7.2 with 4 N sodium hydroxide at times, and a decreased amount of potassium dihydrogen phosphate was added to the reaction mixture. The reaction using ATCC 21477/pHK4 was carried out as a control. After 30 hours of the reaction, the amount of 5'-inosinic acid in the reaction solution was determined through high-performance liquid chromatography.

The results are shown in Table 8. The amount of 5'-inosinic acid accumulated was indicated in terms of the amount of disodium 5'-inosinate 7.5-hydrate. From the results, the conversion of inosine to 5'-inosinic acid was observed in ATCC 21477/pBA-3 which expressed the inosine-guanosine kinase activity.

TABLE 8

| Strain | Amount of 5'-inosinic acid accumulated (g/liter) |
| --- | --- |
| ATCC 21477/pHK4 | not detected |
| ATCC 21477/pBA-3 | 69.8 |

Example 9

Production of 5'-inosinic Acid From Inosine Using the Cells Containing the Inosine-guanosine Kinase Gene of *Exiguobacterium acetylicum*

The cells obtained in Example 8 were suspended in amounts of 200 g/liter in 50 ml of a reaction solution (pH 7.2) containing 60 g/liter of inosine, 20 g/liter of potassium dihydrogen phosphate, 30 g/liter of glucose, 5 g/lite of magnesium sulfate, 10 g/liter of phytic acid (weight ratio of 50%), 1 g/liter of Nymeen S-215 and 1 g/liter of adenine. The suspension was incubated at 32° C. with aerobically stirring. The pH was adjusted to 7.2 with 4 N sodium hydroxide by monitoring using a pH meter, and a decreased amount of potassium dihydrogen phosphate was added to the reaction mixture. After 30 hours of the reaction, the amount of 5'-inosinic acid accumulated was 111.3 g/liter, and the molar yield thereof based on inosine added was approximately 100%.

Example 10

Conversion of Guanosine to 5'-guanylic Acid Using the Cells Containing the Inosine-guanosine Kinase Gene The cells obtained in Example 8 were suspended in amounts of 200 g/liter in 50 ml of a reaction solution (pH 7.2) containing 25 g/liter of guanosine, 20 g/liter of potassium dihydrogen phosphate, 30 g/liter of glucose, 5 g/lite of magnesium sulfate, 10 g/liter of phytic acid (weight ratio of 50%), 4 g/liter of Nymeen S-215 and 1 g/liter of adenine. The suspension was incubated at 32° C. with aerobically stirring. The pH was adjusted to 7.2 with 4 N sodium hydroxide by monitoring using a pH meter. After 8 hours of the reaction, the amount of 5'-guanylic acid accumulated was 7.3 g/liter, and the molar yield thereof based on guanosine added was approximately 14%.

Example 11

Detection of the Inosine-guanosine Kinase Activity in *Exiguobacterium aurantiacum*, *Kurthia gibsonii* and *Kurthia zopfii*

*Exiguobacterium aurantiacum* ATCC 35652 was inoculated in 50 ml of a medium (pH 9.7) containing 1% polypeptone, 1% bacto yeast extract, 0.5% glucose, 0.5% sodium chloride and 1% sodium carbonate. Each of *Kurthia gibsonii* ATCC 43195 and *Kurthia zopfii* ATCC 33403 was inoculated in 50 ml of a medium (pH 7.2) containing 1% polypeptone, 1% bacto yeast extract, 0.5% glucose and 0.5% sodium chloride. The cultivation was carried out at 30° C. for 4 hours. Each of the cultures obtained was centrifuged at 7,000 rpm for 10 minutes, and the precipitate was washed twice with 0.9% sodium chloride to obtain wet cells. The cells were suspended in 3 ml of the buffer A and disrupted by sonication. The suspension was centrifuged at 15,000 rpm for 30 minutes, and the supernatant was desalted using a Sephadex G-25 column (manufactured by-Pharmacia Co.), to obtain approximately 3.5 ml of a crude enzyme extract. Five microliters of the crude enzyme extract were added to 50 µl of 100 mM Tris-hydrochloride buffer (pH 7.5) containing 5 mM magnesium chloride, 5 mM ATP, 100 mM potassium chloride, 0.06 mM guanosine and 0.04 mM [8-$^{14}$C]-guanosine. The mixture was incubated at 30° C. for 10 minutes. The amount of 5'-guanylic acid formed was determined, and the specific activity of the inosine-guanosine kinase was measured. The results are shown in Table 9. The inosine-guanosine kinase activity was observed in all of the strains.

TABLE 9

| Strain | Specific activity (nmol/min/mg · protein) |
| --- | --- |
| Exiguobacterium aurantiacum | 46.3 |
| Kurthia gibsonii | 6.64 |
| Kurthia zopfii | 1.19 |

Example 12

Detection of Fragments Having Homology to the Inosine-guanosine kinase gene of Exiguobacterium acetylicum in chromosomes of Exiguobacterium aurantiacum, Kurthia gibsonii and Kurthia zopfii Exiguobacterium aurantiacum ATCC 35652, Kurthia gibsonii ATCC 3195 and Kurthia zopfii ATCC 33403 were cultured at 30° C. for 16 hours in the same manner as in Example 11. The chromosomal DNAs were prepared from the respective cultures in the same manner as in Example 5 (2). Ten micrograms of each of the chromosomal DNAs and 100 units of restriction endonuclease EcoRI were mixed with 50 mM Tris-hydrochloride buffer (pH 7.5) containing 10 mM magnesium chloride, 100 mM sodium chloride and 1 mM dithiothreitol, and were incubated at 37° C. for 14 hours. Subsequently, the reaction mixture was extracted with phenol and the extract was precipitated with ethanol in a usual manner. The thus obtained chromosomal DNA digested by EcoRI was subjected to 0.8% agarose gel electrophoresis and was transferred onto a nylon membrane (made by DuPont Co.) from the agarose gel by the alkaline transfer method described in Molecular Cloning 2nd edition, by J. Sambrook, E. F. Fritsch and T. Maniatis, Cold Spring Harbour Laboratory Press, p. 9.31 (1989). The membrane was subjected to the hybridization at 42° C. for 14 hours in the presence of 20% formamide using as the probe the fragment containing the inosine-guanosine kinase gene derived from Exiguobacterium acetylicum. When this membrane was washed with 0.2×SSC (0.03 M sodium chloride and 3 mM sodium citrate) and 0.1% SDS, homologous fragments were detected in all of the strains. Especially, the fragment of approximately 4.6 kb which exhibited the strongest homology was detected in the chromosome of Exiguobacterium aurantiacum.

Example 13

Isolation of the Fragment Homologous to the Inosine-guanosine Kinase Gene Derived From Exiguobacterium acetylicum From the Chromosome of Exiguobacterium aurantiacum ATCC 35652

Eighteen micrograms of the chromosomal DNA of Exiguobacterium aurantiacum ATCC 35652 and 200 units of restriction endonuclease EcoRI were reacted at 37° C. for 3 hours. The reaction mixture was extracted with phenol, and the extract was precipitated with ethanol. The resulting digested fragments were subjected to agarose gel electrophoresis. Fragments of approximately 4.6 kb were recovered using a glass powder (made by Takara Shuzo Co.) to obtain the size-selected chromosomal fragments of Exiguobacterium aurantiacum ATCC 35652.

One microgram of plasmid vector pMW218 (made by Nippon Gene Co.) was incubated with 20 units of restriction endonuclease EcoRI at 37° C. for 3 hours. The digest was extracted with phenol, and the extract was precipitated with ethanol. Subsequently, the DNA fragment was dephosphorylated by the alkaline phosphatase treatment. The thus-treated fragment was extracted with phenol, and the extract was precipitated with ethanol.

0.2 µg of this pMW218 digested with EcoRI was ligated with 5 µg of the chromosomal fragments of Exiguobacterium aurantiacum digested with EcoRI using T4 DNA ligase (made by Takara Shuzo Co.). Then, E. coli JM109 (made by Takara Shuzo Co.) was transformed with this DNA mixture, and was inoculated on L-agar plate media containing 100 µg/ml of kanamycin to obtain approximately 1,000 transformants.

From among the transformants obtained, the transformant to be hybridized with the probe DNA was selected by the colony hybridization method. A plasmid DNA was extracted from this transformant by the alkaline lysis method. This plasmid DNA contained a DNA fragment of approximately 4.6 kb derived from the chromosome of Exiguobacterium aurantiacum.

Example 14

Determination of the Nucleotide Sequence of the Inosine-guanosine Kinase Gene Derived From Exiguobacterium aurantiacum The plasmid obtained in Example 13 was cleaved with restriction endonucleases, and was then subjected to the Southern hybridization, thereby identifying the fragment to be hybridized with the probe DNA. As a result, it was found that a fragment of approximately 2.7 kb which was cleaved with EcoRI and PstI was hybridized. This DNA fragment was ligated-with plasmid vector pSTV28 (made by Takara Shuzo Co.) cleaved with EcoRI and PstI, and introduced into E. coli JM109. From among the transformants obtained, the fragment to be hybridized with the probe DNA was cloned by the colony hybridization method described in Molecular Cloning 2nd edition, by J. Sambrook, E. F. Fritsch and T. Maniatis, Cold Spring Harbour Laboratory Press, p. 1.90 (1989). The inosine-guanosine kinase activity of the cell free extract of an E. coli strain harboring a plasmid containing the above-fragment was measured according to the method described in Example 7 (5), and it was found to be approximately 300 times as high as the strain harboring the vector which was used for reference. Thus it was confirmed that the cloned fragment contains the inosine-guanosine kinase gene derived from Exiguobacterium aurantiacum.

The nucleotide sequence of the fragment cleaved with EcoRI and PstI was determined using the thus-obtained plasmid DNA. The nucleotide sequence of the open reading frame to be presumed from the determined nucleotide sequence is represented by SEQ ID NO:16 in Sequence Listing. The amino acid sequence of the product to be presumed from this nucleotide sequence is represented by SEQ ID NO:17 in Sequence Listing. Both of the nucleotide sequence and the amino acid sequence showed a strong homology to the inosine-guanosine kinase derived from *Exiguobacterium acetylicum*. However, the gene was no doubt a novel gene. That is, the gene encoding the protein having the amino acid sequence represented by SEQ ID NO:15 in Sequence Listing is the inosine-guanosine kinase gene of *Exiguobacterium aurantiacum* ATCC 35652.

As mentioned above, a gene capable of hybridizing the inosine-guanosine kinase gene derived from *Exiguobacterium acetylicum* was obtained, and it was confirmed that this gene encodes a protein having the inosine-guanosine kinase activity.

What is claimed is:

1. A process for producing 5'-inosinic acid or 5'-guanylic acid, which comprises contacting inosine or guanosine or a precursor thereof with a transformant obtained by introducing a gene encoding a protein comprising SEQ ID NO: 3 or 17 having inosine-guanosine kinase activity into microorganism capable of regenerating ATP consumed in the process, an energy source and a phosphate group donor, accumulating 5'-inosinic acid or 5'-guanylic acid in the reaction solution, and collecting the same therefrom, where the phosphate group donor is an inorganic phosphoric acid, a salt of an inorganic phosphoric acid, phenyl phosphate, acetyl phosphate or carbamyl phosphate.

2. The process for producing 5'-inosinic acid or 5'-guanylic acid according to claim 1, wherein the microorganism capable of regenerating ATP belongs to a genus selected from the group consisting of Corynebacterium, Escherichia, Saccharomyces, Staphylococcus and Candida.

3. The process for producing 5'-inosinic acid or 5'-guanylic acid according to claim 1, wherein the microorganism capable of regenerating ATP belongs to *Corynebacterium ammoniagenes*.

4. The process for producing 5'-inosinic acid or 5'-guanylic acid according to any one of claims 1 to 3, wherein the gene encoding the protein having inosine-guanosine kinase activity is a gene derived from *Exiguobacterium acetylicum*.

5. The process for producing 5'-inosinic acid or 5'-guanylic acid according to claim 3, wherein the gene encoding the protein having inosine-guanosine kinase activity is a gene derived from *Exiguobacterium acetylicum*.

6. A process for producing 5'-inosinic acid or 5'-guanylic acid, which comprises contacting inosine or guanosine or a precursor thereof with a transformant obtained by introducing (a) a gene encoding a protein having inosine-guanosine kinase activity into (b) a microorganism capable of regenerating ATP consumed in the process, an energy source and a phosphate group donor, accumulating 5'-inosinic acid or 5'-guanylic acid in the reaction solution, and collecting the same therefrom, where the phosphate group donor is an inorganic phosphoric acid, a salt of an inorganic phosphoric acid, phenyl phosphate, acetyl phosphate or carbamyl phosphate, wherein the gene (a) is a gene having the sequence of SEQ ID NO:1, wherein said transformant is the only microorganism employed in the stated process.

7. A process according to claim 6, wherein the gene (a) is the gene having SEQ ID NO:1.

* * * * *